United States Patent
Ossendorp et al.

(10) Patent No.: US 9,770,506 B2
(45) Date of Patent: *Sep. 26, 2017

(54) ADJUVANT COMPOUND

(71) Applicant: ISA Pharmaceuticals B.V., Leiden (NL)

(72) Inventors: Ferdinand Antonius Ossendorp, Amstelveen (NL); Cornelis Johannes Maria Melief, Haarlem (NL); Selina Khan, Leiden (NL); Dmitri Viktorovitsj Filippov, Leiden (NL); Gijsbert Arie Van der Marel, Leiden (NL)

(73) Assignee: ISA Pharmaceuticals, B.V., Leiden (NL)

( * ) Notice: Subject to any disclaimer, the term of this patent is extended or adjusted under 35 U.S.C. 154(b) by 24 days.

This patent is subject to a terminal disclaimer.

(21) Appl. No.: 15/062,589

(22) Filed: Mar. 7, 2016

(65) Prior Publication Data

US 2016/0250325 A1  Sep. 1, 2016

Related U.S. Application Data

(63) Continuation of application No. 14/349,652, filed as application No. PCT/NL2012/050694 on Oct. 4, 2012, now Pat. No. 9,314,521.

(60) Provisional application No. 61/543,510, filed on Oct. 5, 2011, provisional application No. 61/615,566, filed on Mar. 26, 2012.

Foreign Application Priority Data

Oct. 5, 2011  (NL) ..................... 2007536

(51) Int. Cl.
| | |
|---|---|
| *A61K 39/39* | (2006.01) |
| *C07K 7/04* | (2006.01) |
| *A61K 47/48* | (2006.01) |
| *C07K 7/06* | (2006.01) |
| *A61K 39/00* | (2006.01) |

(52) U.S. Cl.
CPC .............. *A61K 39/39* (2013.01); *A61K 47/48* (2013.01); *A61K 47/48238* (2013.01); *A61K 47/48376* (2013.01); *C07K 7/04* (2013.01); *C07K 7/06* (2013.01); *A61K 2039/55511* (2013.01); *A61K 2039/55516* (2013.01)

(58) Field of Classification Search
None
See application file for complete search history.

(56) References Cited

FOREIGN PATENT DOCUMENTS

| EP | 0 431 327 A1 | 6/1991 |
|---|---|---|
| WO | WO-2008/021295 | 2/2008 |
| WO | WO-2009/072767 | 6/2009 |

OTHER PUBLICATIONS

Spohn et al., Vaccine 22 (2004) 2494-2499.*
Itoh et al., "Synthesis and structure-activity relationships of TAN-1511 analogues as potent hematopoietic agents", Chem. Pharm. Bull., Feb. 1998, vol. 46, No. 2 pp. 255-273.
International Search Report issued in International Patent Application No. PCT/NL2012/050694 mailed Dec. 20, 2012.
Mi Sun Jin et al., "Crystal Structure of the TLR1-TLR2 Heterodimer Induced by Binding of a Tri-Acylated Lipopeptide," Cell, vol. 130, No. 6, pp. 1071-1082.
Moyle, Peter et al., "Self-adjuvanting lipopeptide vaccines", Current Medicinal Chemistry, Bentham Science Publishers BV, BE, vol. 15, No. 5, Jan. 1, 2008, pp. 506-516.
Schroder, et al. "Identification of Diacylated Ureas as a Novel Family of Fungus-specific Leukocyte-activating Pathogen-associated Molecules", The Journal of Biological Chemistry (Aug. 2, 2002) vol. 277, No. 31, pp. 27887-27895.

(Continued)

*Primary Examiner* — Marcela M Cordero Garcia
*Assistant Examiner* — Catherine Mader
(74) *Attorney, Agent, or Firm* — Gilberto M. Villacorta; Sunit Talapatra; Foley & Lardner LLP

(57) ABSTRACT

The invention is directed to a compound according to the formula [1]

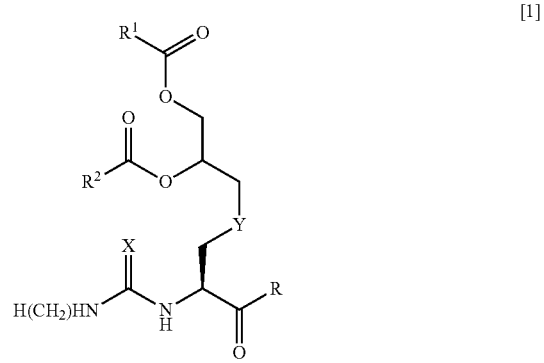

wherein $R^1$ and $R^2$ are branched or straight groups having up to 17 atoms selected from carbon, nitrogen, oxygen and sulphur, n is 0 to and including 18, Y is sulphur or selene, X is S or O and R is —OH or an organic group comprising one or more peptides, one or more nucleic acids, one or more antibodies or combinations thereof. The invention is also directed to process for preparing said compound and the use of said compound as an adjuvant. The invention is also directed to a composition comprising said compound and the use of said composition, for example as a vaccine composition.

21 Claims, 6 Drawing Sheets

(56) References Cited

OTHER PUBLICATIONS

Spohn, et al. "Synthetic lipopeptide adjuvants and Toll-like receptor s-structure-activity relationships", Vaccine (2004) vol. 22, pp. 2494-2499.
Tsuneaki, Hida et al., "Synthesis and Biological Activities of TAN-1511 analogues", Journal of Antibiotics, vol. 48, No. 7, Jan. 1, 1995, pp. 589-603.
Zeng et al., "Lipidation of intact proteins produces highly immunogenic vaccine candidates," Mol Imunnol, Jan. 2011, vol. 48, No. 4, pp. 490-496.

\* cited by examiner

SEQUENCE LISTING

<160> NUMBER OF SEQ ID NOS: 28

<210> SEQ ID NO 1
<211> LENGTH: 365
<212> TYPE: PRT
<213> ORGANISM: Homo sapiens

<400> SEQUENCE: 1

```
Met Glu Thr Leu Cys Gln Arg Leu Asn Val Cys Gln Asp Lys Ile Leu
1               5                   10                  15

Thr His Tyr Glu Asn Asp Ser Thr Asp Leu Arg Asp His Ile Asp Tyr
            20                  25                  30

Trp Lys His Met Arg Leu Glu Cys Ala Ile Tyr Tyr Lys Ala Arg Glu
        35                  40                  45

Met Gly Phe Lys His Ile Asn His Gln Val Val Pro Thr Leu Ala Val
50                  55                  60

Ser Lys Asn Lys Ala Leu Gln Ala Ile Glu Leu Gln Leu Thr Leu Glu
65                  70                  75                  80

Thr Ile Tyr Asn Ser Gln Tyr Ser Asn Glu Lys Trp Thr Leu Gln Asp
            85                  90                  95

Val Ser Leu Glu Val Tyr Leu Thr Ala Pro Thr Gly Cys Ile Lys Lys
        100                 105                 110

His Gly Tyr Thr Val Glu Val Gln Phe Asp Gly Asp Ile Cys Asn Thr
    115                 120                 125

Met His Tyr Thr Asn Trp Thr His Ile Tyr Ile Cys Glu Glu Ala Ser
130                 135                 140

Val Thr Val Val Glu Gly Gln Val Asp Tyr Tyr Gly Leu Tyr Tyr Val
145                 150                 155                 160

His Glu Gly Ile Arg Thr Tyr Phe Val Gln Phe Lys Asp Asp Ala Glu
            165                 170                 175

Lys Tyr Ser Lys Asn Lys Val Trp Glu Val His Ala Gly Gly Gln Val
        180                 185                 190

Ile Leu Cys Pro Thr Ser Val Phe Ser Ser Asn Glu Val Ser Ser Pro
    195                 200                 205

Glu Ile Ile Arg Gln His Leu Ala Asn His Pro Ala Ala Thr His Thr
210                 215                 220

Lys Ala Val Ala Leu Gly Thr Glu Glu Thr Gln Thr Thr Ile Gln Arg
225                 230                 235                 240

Pro Arg Ser Glu Pro Asp Thr Gly Asn Pro Cys His Thr Thr Lys Leu
            245                 250                 255

Leu His Arg Asp Ser Val Asp Ser Ala Pro Ile Leu Thr Ala Phe Asn
        260                 265                 270

Ser Ser His Lys Gly Arg Ile Asn Cys Asn Ser Asn Thr Thr Pro Ile
    275                 280                 285

Val His Leu Lys Gly Asp Ala Asn Thr Leu Lys Cys Leu Arg Tyr Arg
290                 295                 300

Phe Lys Lys His Cys Thr Leu Tyr Thr Ala Val Ser Ser Thr Trp His
305                 310                 315                 320

Trp Thr Gly His Asn Val Lys His Lys Ser Ala Ile Val Thr Leu Thr
            325                 330                 335

Tyr Asp Ser Glu Trp Gln Arg Asp Gln Phe Leu Ser Gln Val Lys Ile
        340                 345                 350

Pro Lys Thr Ile Thr Val Ser Thr Gly Phe Met Ser Ile
    355                 360                 365
```

<210> SEQ ID NO 2
<211> LENGTH: 158
<212> TYPE: PRT
<213> ORGANISM: Homo sapiens

<400> SEQUENCE: 2

```
Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
                20                  25                  30

Ile Ile Leu Glu Cys Val Tyr Cys Lys Gln Gln Leu Leu Arg Arg Glu
            35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
                100                 105                 110

Cys Gln Lys Pro Leu Cys Pro Glu Glu Lys Gln Arg His Leu Asp Lys
            115                 120                 125

Lys Gln Arg Phe His Asn Ile Arg Gly Arg Trp Thr Gly Arg Cys Met
130                 135                 140

Ser Cys Cys Arg Ser Ser Arg Thr Arg Arg Glu Thr Gln Leu
145                 150                 155

<210> SEQ ID NO 3
<211> LENGTH: 98
<212> TYPE: PRT
<213> ORGANISM: Homo sapiens

<400> SEQUENCE: 3

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 4
<211> LENGTH: 365
<212> TYPE: PRT
<213> ORGANISM: Homo sapiens

<400> SEQUENCE: 4

Met Gln Thr Pro Lys Glu Thr Leu Ser Glu Arg Leu Ser Cys Val Gln
1               5                   10                  15

Asp Lys Ile Ile Asp His Tyr Glu Asn Asp Ser Lys Asp Ile Asp Ser
                20                  25                  30

Gln Ile Gln Tyr Trp Gln Leu Ile Arg Trp Glu Asn Ala Ile Phe Phe
            35                  40                  45

Ala Ala Arg Glu His Gly Ile Gln Thr Leu Asn His Gln Val Val Pro
    50                  55                  60

Ala Tyr Asn Ile Ser Lys Ser Lys Ala His Lys Ala Ile Glu Leu Gln
```

```
                65                  70                  75                  80
Met Ala Leu Gln Gly Leu Ala Gln Ser Arg Tyr Lys Thr Glu Asp Trp
                    85                  90                  95

Thr Leu Gln Asp Thr Cys Glu Glu Leu Trp Asn Thr Glu Pro Thr His
                100                 105                 110

Cys Phe Lys Lys Gly Gly Gln Thr Val Gln Val Tyr Phe Asp Gly Asn
                115                 120                 125

Lys Asp Asn Cys Met Thr Tyr Val Ala Trp Asp Ser Val Tyr Tyr Met
            130                 135                 140

Thr Asp Ala Gly Thr Trp Asp Lys Thr Ala Thr Cys Val Ser His Arg
145                 150                 155                 160

Gly Leu Tyr Tyr Val Lys Glu Gly Tyr Asn Thr Phe Tyr Ile Glu Phe
                165                 170                 175

Lys Ser Glu Cys Glu Lys Tyr Gly Asn Thr Gly Thr Trp Glu Val His
                180                 185                 190

Phe Gly Asn Asn Val Ile Asp Cys Asn Asp Ser Met Cys Ser Thr Ser
            195                 200                 205

Asp Asp Thr Val Ser Ala Thr Gln Leu Val Lys Gln Leu Gln His Thr
        210                 215                 220

Pro Ser Pro Tyr Ser Ser Thr Val Ser Val Gly Thr Ala Lys Thr Tyr
225                 230                 235                 240

Gly Gln Thr Ser Ala Ala Thr Arg Pro Gly His Cys Gly Leu Ala Glu
                245                 250                 255

Lys Gln His Cys Gly Pro Val Asn Pro Leu Leu Gly Ala Ala Thr Pro
                260                 265                 270

Thr Gly Asn Asn Lys Arg Arg Lys Leu Cys Ser Gly Asn Thr Thr Pro
            275                 280                 285

Ile Ile His Leu Lys Gly Asp Arg Asn Ser Leu Lys Cys Leu Arg Tyr
        290                 295                 300

Arg Leu Arg Lys His Ser Asp His Tyr Arg Asp Ile Ser Ser Thr Trp
305                 310                 315                 320

His Trp Thr Gly Ala Gly Asn Glu Lys Thr Gly Ile Leu Thr Val Thr
                325                 330                 335

Tyr His Ser Glu Thr Gln Arg Thr Lys Phe Leu Asn Thr Val Ala Ile
                340                 345                 350

Pro Asp Ser Val Gln Ile Leu Val Gly Tyr Met Thr Met
                355                 360                 365

<210> SEQ ID NO 5
<211> LENGTH: 158
<212> TYPE: PRT
<213> ORGANISM: Homo sapiens

<400> SEQUENCE: 5

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
                20                  25                  30

Val Tyr Cys Lys Thr Val Leu Glu Leu Thr Glu Val Phe Glu Phe Ala
            35                  40                  45

Phe Lys Asp Leu Phe Val Val Tyr Arg Asp Ser Ile Pro His Ala Ala
        50                  55                  60

Cys His Lys Cys Ile Asp Phe Tyr Ser Arg Ile Arg Glu Leu Arg His
65                  70                  75                  80
```

```
Tyr Ser Asp Ser Val Tyr Gly Asp Thr Leu Glu Lys Leu Thr Asn Thr
                 85                  90                  95

Gly Leu Tyr Asn Leu Leu Ile Arg Cys Leu Arg Cys Gln Lys Pro Leu
            100                 105                 110

Asn Pro Ala Glu Lys Leu Arg His Leu Asn Glu Lys Arg Arg Phe His
            115                 120                 125

Asn Ile Ala Gly His Tyr Arg Gly Gln Cys His Ser Cys Cys Asn Arg
            130                 135                 140

Ala Arg Gln Glu Arg Leu Gln Arg Arg Glu Thr Gln Val
145                 150                 155

<210> SEQ ID NO 6
<211> LENGTH: 105
<212> TYPE: PRT
<213> ORGANISM: Homo sapiens

<400> SEQUENCE: 6

Met His Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
            20                  25                  30

Asp Ser Glu Glu Glu Asn Asp Glu Ile Asp Gly Val Asn His Gln His
            35                  40                  45

Leu Pro Ala Arg Arg Ala Glu Pro Gln Arg His Thr Met Leu Cys Met
50                  55                  60

Cys Cys Lys Cys Glu Ala Arg Ile Glu Leu Val Val Glu Ser Ser Ala
65                  70                  75                  80

Asp Asp Leu Arg Ala Phe Gln Gln Leu Phe Leu Asn Thr Leu Ser Phe
            85                  90                  95

Val Cys Pro Trp Cys Ala Ser Gln Gln
            100                 105

<210> SEQ ID NO 7
<211> LENGTH: 393
<212> TYPE: PRT
<213> ORGANISM: Homo sapiens

<400> SEQUENCE: 7

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
            35                  40                  45

Asp Ile Glu Gln Trp Phe Thr Glu Asp Pro Gly Pro Asp Glu Ala Pro
50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
            85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
            130                 135                 140
```

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390

<210> SEQ ID NO 8
<211> LENGTH: 509
<212> TYPE: PRT
<213> ORGANISM: Homo sapiens

<400> SEQUENCE: 8

Met Glu Arg Arg Arg Leu Trp Gly Ser Ile Gln Ser Arg Tyr Ile Ser
1               5                   10                  15

Met Ser Val Trp Thr Ser Pro Arg Arg Leu Val Glu Leu Ala Gly Gln
                20                  25                  30

Ser Leu Leu Lys Asp Glu Ala Leu Ala Ile Ala Ala Leu Glu Leu Leu
            35                  40                  45

Pro Arg Glu Leu Phe Pro Pro Leu Phe Met Ala Ala Phe Asp Gly Arg
        50                  55                  60

His Ser Gln Thr Leu Lys Ala Met Val Gln Ala Trp Pro Phe Thr Cys
65                  70                  75                  80

Leu Pro Leu Gly Val Leu Met Lys Gly Gln His Leu His Leu Glu Thr
                85                  90                  95

Phe Lys Ala Val Leu Asp Gly Leu Asp Val Leu Leu Ala Gln Glu Val
            100                 105                 110

Arg Pro Arg Arg Trp Lys Leu Gln Val Leu Asp Leu Arg Lys Asn Ser
        115                 120                 125

-continued

```
His Gln Asp Phe Trp Thr Val Trp Ser Gly Asn Arg Ala Ser Leu Tyr
            130                 135                 140
Ser Phe Pro Glu Pro Glu Ala Ala Gln Pro Met Thr Lys Lys Arg Lys
145                 150                 155                 160
Val Asp Gly Leu Ser Thr Glu Ala Glu Gln Pro Phe Ile Pro Val Glu
                165                 170                 175
Val Leu Val Asp Leu Phe Leu Lys Glu Gly Ala Cys Asp Glu Leu Phe
                180                 185                 190
Ser Tyr Leu Ile Glu Lys Val Lys Arg Lys Lys Asn Val Leu Arg Leu
            195                 200                 205
Cys Cys Lys Lys Leu Lys Ile Phe Ala Met Pro Met Gln Asp Ile Lys
    210                 215                 220
Met Ile Leu Lys Met Val Gln Leu Asp Ser Ile Glu Asp Leu Glu Val
225                 230                 235                 240
Thr Cys Thr Trp Lys Leu Pro Thr Leu Ala Lys Phe Ser Pro Tyr Leu
                245                 250                 255
Gly Gln Met Ile Asn Leu Arg Arg Leu Leu Leu Ser His Ile His Ala
                260                 265                 270
Ser Ser Tyr Ile Ser Pro Glu Lys Glu Glu Gln Tyr Ile Ala Gln Phe
            275                 280                 285
Thr Ser Gln Phe Leu Ser Leu Gln Cys Leu Gln Ala Leu Tyr Val Asp
    290                 295                 300
Ser Leu Phe Phe Leu Arg Gly Arg Leu Asp Gln Leu Leu Arg His Val
305                 310                 315                 320
Met Asn Pro Leu Glu Thr Leu Ser Ile Thr Asn Cys Arg Leu Ser Glu
                325                 330                 335
Gly Asp Val Met His Leu Ser Gln Ser Pro Ser Val Ser Gln Leu Ser
                340                 345                 350
Val Leu Ser Leu Ser Gly Val Met Leu Thr Asp Val Ser Pro Glu Pro
            355                 360                 365
Leu Gln Ala Leu Leu Glu Arg Ala Ser Ala Thr Leu Gln Asp Leu Val
    370                 375                 380
Phe Asp Glu Cys Gly Ile Thr Asp Asp Gln Leu Leu Ala Leu Leu Pro
385                 390                 395                 400
Ser Leu Ser His Cys Ser Gln Leu Thr Thr Leu Ser Phe Tyr Gly Asn
                405                 410                 415
Ser Ile Ser Ile Ser Ala Leu Gln Ser Leu Leu Gln His Leu Ile Gly
                420                 425                 430
Leu Ser Asn Leu Thr His Val Leu Tyr Pro Val Pro Leu Glu Ser Tyr
            435                 440                 445
Glu Asp Ile His Gly Thr Leu His Leu Glu Arg Leu Ala Tyr Leu His
    450                 455                 460
Ala Arg Leu Arg Glu Leu Leu Cys Glu Leu Gly Arg Pro Ser Met Val
465                 470                 475                 480
Trp Leu Ser Ala Asn Pro Cys Pro His Cys Gly Asp Arg Thr Phe Tyr
                485                 490                 495
Asp Pro Glu Pro Ile Leu Cys Pro Cys Phe Met Pro Asn
                500                 505
```

<210> SEQ ID NO 9
<211> LENGTH: 750
<212> TYPE: PRT
<213> ORGANISM: Homo sapiens

```
<400> SEQUENCE: 9

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
                35                  40                  45

Ala Thr Asn Ile Thr Pro Lys His Asn Met Lys Ala Phe Leu Asp Glu
50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
                100                 105                 110

Tyr Asp Val Leu Leu Ser Tyr Pro Asn Lys Thr His Pro Asn Tyr Ile
                115                 120                 125

Ser Ile Ile Asn Glu Asp Gly Asn Glu Ile Phe Asn Thr Ser Leu Phe
130                 135                 140

Glu Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
                180                 185                 190

Lys Ile Asn Cys Ser Gly Lys Ile Val Ile Ala Arg Tyr Gly Lys Val
                195                 200                 205

Phe Arg Gly Asn Lys Val Lys Asn Ala Gln Leu Ala Gly Ala Lys Gly
                210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
                245                 250                 255

Asn Ile Leu Asn Leu Asn Gly Ala Gly Asp Pro Leu Thr Pro Gly Tyr
                260                 265                 270

Pro Ala Asn Glu Tyr Ala Tyr Arg Arg Gly Ile Ala Glu Ala Val Gly
                275                 280                 285

Leu Pro Ser Ile Pro Val His Pro Ile Gly Tyr Tyr Asp Ala Gln Lys
290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
                340                 345                 350

Thr Arg Ile Tyr Asn Val Ile Gly Thr Leu Arg Gly Ala Val Glu Pro
                355                 360                 365

Asp Arg Tyr Val Ile Leu Gly Gly His Arg Asp Ser Trp Val Phe Gly
                370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415
```

```
Leu Phe Ala Ser Trp Asp Ala Glu Glu Phe Gly Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Gly Lys Ser Leu Tyr Glu Ser
            485                 490                 495

Trp Thr Lys Lys Ser Pro Ser Pro Glu Phe Ser Gly Met Pro Arg Ile
        500                 505                 510

Ser Lys Leu Gly Ser Gly Asn Asp Phe Glu Val Phe Phe Gln Arg Leu
    515                 520                 525

Gly Ile Ala Ser Gly Arg Ala Arg Tyr Thr Lys Asn Trp Glu Thr Asn
        530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
        595                 600                 605

Asp Lys Ile Tyr Ser Ile Ser Met Lys His Pro Gln Glu Met Lys Thr
    610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
        675                 680                 685

His Val Ile Tyr Ala Pro Ser Ser His Asn Lys Tyr Ala Gly Glu Ser
    690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
            740                 745                 750

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tcgtcgtttt gtcgttttgt cgtt                                           24

<210> SEQ ID NO 11
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pam3Cys

<400> SEQUENCE: 11

Cys Ser Lys Lys Lys Lys
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Ile Ile Asn Phe Glu Lys Leu
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Ser Asn Ala Ser Lys Lys Lys Lys
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Arg Arg Arg Arg Arg Arg Arg
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 15

Arg Pro Asp Arg Tyr
1               5

<210> SEQ ID NO 16
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 16

Gln Pro Asp Arg Tyr
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (2)..(6)
<223> OTHER INFORMATION: This region may encompass 1 to 5 "Lys"
      residues, wherein some positions may be absent

<400> SEQUENCE: 17

Ser Lys Lys Lys Lys Lys
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Lys Lys Lys Lys
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: This sequence may encompass 1 to 5 "Lys"
      residues, wherein some positions may be absent

<400> SEQUENCE: 19

Lys Lys Lys Lys Lys
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (1)..(1)
<223> OTHER INFORMATION: Ser(tBu)
<220> FEATURE:
<221> NAME/KEY: MOD_RES
```

```
<222> LOCATION: (2)..(5)
<223> OTHER INFORMATION: Lys(Boc)
<220> FEATURE:
<223> OTHER INFORMATION: C-term Rink Tentagel

<400> SEQUENCE: 20

Ser Lys Lys Lys Lys
1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Fmoc
<220> FEATURE:
<221> NAME/KEY: MOD_RES
<222> LOCATION: (1)..(1)
<223> OTHER INFORMATION: Cys((RS)-2,3-di(palmitoyloxy)-propyl)
<220> FEATURE:
<221> NAME/KEY: MOD_RES
<222> LOCATION: (2)..(2)
<223> OTHER INFORMATION: Ser(tBu)
<220> FEATURE:
<221> NAME/KEY: MOD_RES
<222> LOCATION: (3)..(6)
<223> OTHER INFORMATION: Lys(Boc)

<400> SEQUENCE: 21

Cys Ser Lys Lys Lys Lys
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 1-tetradecyl-urea
<220> FEATURE:
<221> NAME/KEY: MOD_RES
<222> LOCATION: (1)..(1)
<223> OTHER INFORMATION: Cys((RS)-2,3-di(palmitoyloxy)-propyl)
<220> FEATURE:
<223> OTHER INFORMATION: C-term NH2

<400> SEQUENCE: 22

Cys Ser Lys Lys Lys Lys
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 1-dodecadecyl-urea
<220> FEATURE:
<221> NAME/KEY: MOD_RES
<222> LOCATION: (1)..(1)
<223> OTHER INFORMATION: Cys((RS)-2,3-di(palmitoyloxy)-propyl)
<220> FEATURE:
<223> OTHER INFORMATION: C-term NH2

<400> SEQUENCE: 23
```

```
Cys Ser Lys Lys Lys Lys
1               5
```

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (1)..(1)
<223> OTHER INFORMATION: Abu
<220> FEATURE:
<221> NAME/KEY: MOD_RES
<222> LOCATION: (2)..(5)
<223> OTHER INFORMATION: Lys(Boc)
<220> FEATURE:
<223> OTHER INFORMATION: C-term Rink Tentagel

<400> SEQUENCE: 24

```
Xaa Lys Lys Lys Lys
1               5
```

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (1)..(1)
<223> OTHER INFORMATION: Ser(OtBu)
<220> FEATURE:
<221> NAME/KEY: MOD_RES
<222> LOCATION: (2)..(5)
<223> OTHER INFORMATION: Lys(Boc)
<220> FEATURE:
<223> OTHER INFORMATION: C-term Rink Tentagel

<400> SEQUENCE: 25

```
Ser Lys Lys Lys Lys
1               5
```

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 26

```
Xaa Lys Lys Lys Lys
1               5
```

```
<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pam3Cys
<220> FEATURE:
<221> NAME/KEY: MOD_RES
<222> LOCATION: (7)..(8)
<223> OTHER INFORMATION: Aca
<220> FEATURE:
<223> OTHER INFORMATION: C-term Biotin

<400> SEQUENCE: 27

Cys Ser Lys Lys Lys Lys Xaa Xaa
1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 1-tetradecyl-urea
<220> FEATURE:
<221> NAME/KEY: MOD_RES
<222> LOCATION: (1)..(1)
<223> OTHER INFORMATION: Cys((RS)-2,3-di(palmitoyloxy)-propyl)
<220> FEATURE:
<221> NAME/KEY: MOD_RES
<222> LOCATION: (2)..(2)
<223> OTHER INFORMATION: Abu
<220> FEATURE:
<223> OTHER INFORMATION: C-term NH2

<400> SEQUENCE: 28

Cys Xaa Lys Lys Lys Lys
1               5
```

ADJUVANT COMPOUND

CROSS-REFERENCE TO RELATED APPLICATIONS

This application is a Continuation of U.S. patent application Ser. No. 14/349,652, filed Apr. 3, 2014, which is the National Phase of International Patent Application No. PCT/NL2012/050694, filed Oct. 4, 2012, published as WO 2013/051936, which claims priority to Netherlands Application No. 2007536, filed Oct. 5, 2011, U.S. Provisional Application No. 61/543,510, filed Oct. 5, 2011 and U.S. Provisional Application No. 61/615,566, filed Mar. 26, 2012. The contents of these applications are herein incorporated by reference in their entirety.

SEQUENCE LISTING

The instant application contains a Sequence Listing which has been submitted in ASCII format via EFS-WEB and is hereby incorporated by reference in its entirety. Said ASCII copy, created on Mar. 1, 2016, is named SequenceListing.txt and is 31 KB.

FIELD OF THE INVENTION

The present invention relates to a novel compound suited as adjuvant in a vaccine composition, a process to prepare the compound and a composition comprising the compound.

BACKGROUND OF THE INVENTION

Vaccination strategies have been used for decades primarily to foster a protective immunity to protect patients from developing a disease after contact with an infectious agent. To this end live attenuated, dead or disrupted pathogens, pathogen preparations, or purified or recombinant components of the pathogens have been administered to patients to elicit a specific immune response to antigenic components of the respective pathogen. The components, which stimulate such an immune response can be, for example, pathogen specific proteins, polysaccharides or lipids. The specific immune response against antigens comprised within pathogens can be further stimulated by the co-administration of adjuvants. Adjuvants are known in the art to accelerate, prolong, or enhance the quality of the specific immune response to the antigen or antigens and are currently employed as part of vaccines. The proposed advantages of adjuvants include their ability to: 1) direct and optimize immune responses that are appropriate for the vaccine; 2) enable mucosal delivery of vaccines; 3) promote cell-mediated immune response; 4) enhance the immunogenicity of weaker immunogens such as highly purified or recombinant antigens; 5) reduce the amount of antigen or the frequency of immunization required to provide protective immunity; 6) improve efficacy of vaccines in individuals with reduced or weakened immune responses such as newborns, the aged, and immunocompromized patients.

Adjuvants have diverse mechanisms of action. One set of adjuvants act through toll-like receptors. Toll-like receptors (TLR) recognize specific patterns of microbial components, especially those from pathogens, and regulate the activation of both innate and adaptive immunity. Immature dendritic cells mature in response to these microbial components. As of yet, 13 members of the TLR-family have been identified. TLR are expressed by phagocytic cells such as monocytes, macrophages and dendritic cells. TLR activation through ligand binding leads to signal transduction events either in a MyD88-dependent pathway (NF-[kappa]β) or MyD88-independent pathway (IFR-3). A known lipopeptide adjuvant which interacts with toll-like receptor 2 (TLR2) is the so-called Pam3Cys-lipopeptide. According to Renate Spohn et al. (Vaccine 22 (2004) 2494-2499), the Pam3Cys-SK4 variant was found to be the most effective additive for electing a cellular immune response in mice. Another advantage of Pam3Cys-SK4 is that it is chemically stable and can be produced in large quantities at high quality. A Pam3Cys-lipopeptide, Pam3Cys-Ser-(Lys)4(Aca-Aca-Biotin).2trifluoroacetate is commercially available from for example Enzo Life Sciences International Inc, Plymouth Meeting, Pa., USA for use as an adjuvant.

WO-A-2009/072767 describes the use of a mixture of the Pam3Cys-SK4 and polyinosinic:polycytidylic acid as adjuvant for a vaccine.

The object of the present invention is to improve the immune response of a Pam3Cys-like lipopeptide.

SUMMARY OF THE INVENTION

The present invention is directed to an improved Pam3Cys-like lipopeptide, inducing a better immune response. The new compound is represented by

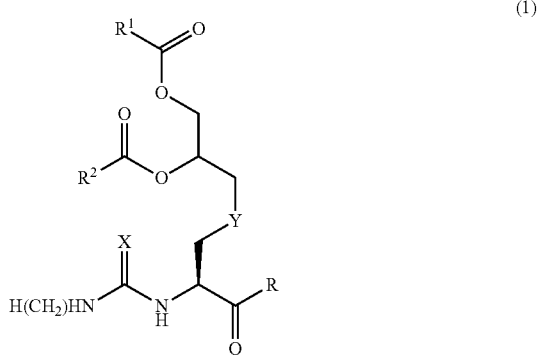

(1)

wherein $R^1$ and $R^2$ are each independently a branched or straight group having up to 17 atoms selected from carbon, nitrogen, oxygen and sulphur, n is 0 to and including 18, Y is sulphur or selene, X is S or O and R is —OH or an organic group comprising one or more peptides, one or more nucleic acids, one or more antibodies or combinations thereof. Preferably, $R^1$ and $R^2$ are each independently branched or straight alkyl groups having up to 17 carbon atoms, preferably 10 tot 17 carbon atoms. Preferably, $R^1$ and $R^2$ are each independently branched or straight alkyl groups having up to 17 carbon atoms, preferably 10 to 17 carbon atoms, and Y is sulphur.

Applicants found that the compound according to the invention is able to induce an improved immune response by functionally stimulating TLR2 as compared to the known Pam3Cys-SK4. Without wishing to be bound to the following theory, applicants believe that the higher stimulation level is achieved by exchanging the bridging —CH₂-group in the N-terminal palmitoyl moiety of the known compound into a —NH-bridging group. The fatty chains of the compound fit in the defined pockets in the dimeric receptor and it is believed that by incorporating the bridging —NH—group, a hydrogen bridge is created. This results in a tighter binding of the ligand to the receptor, which in turn is beneficial to achieve the desired adjuvant activity.

DETAILED DESCRIPTION OF THE INVENTION

Figure 1:
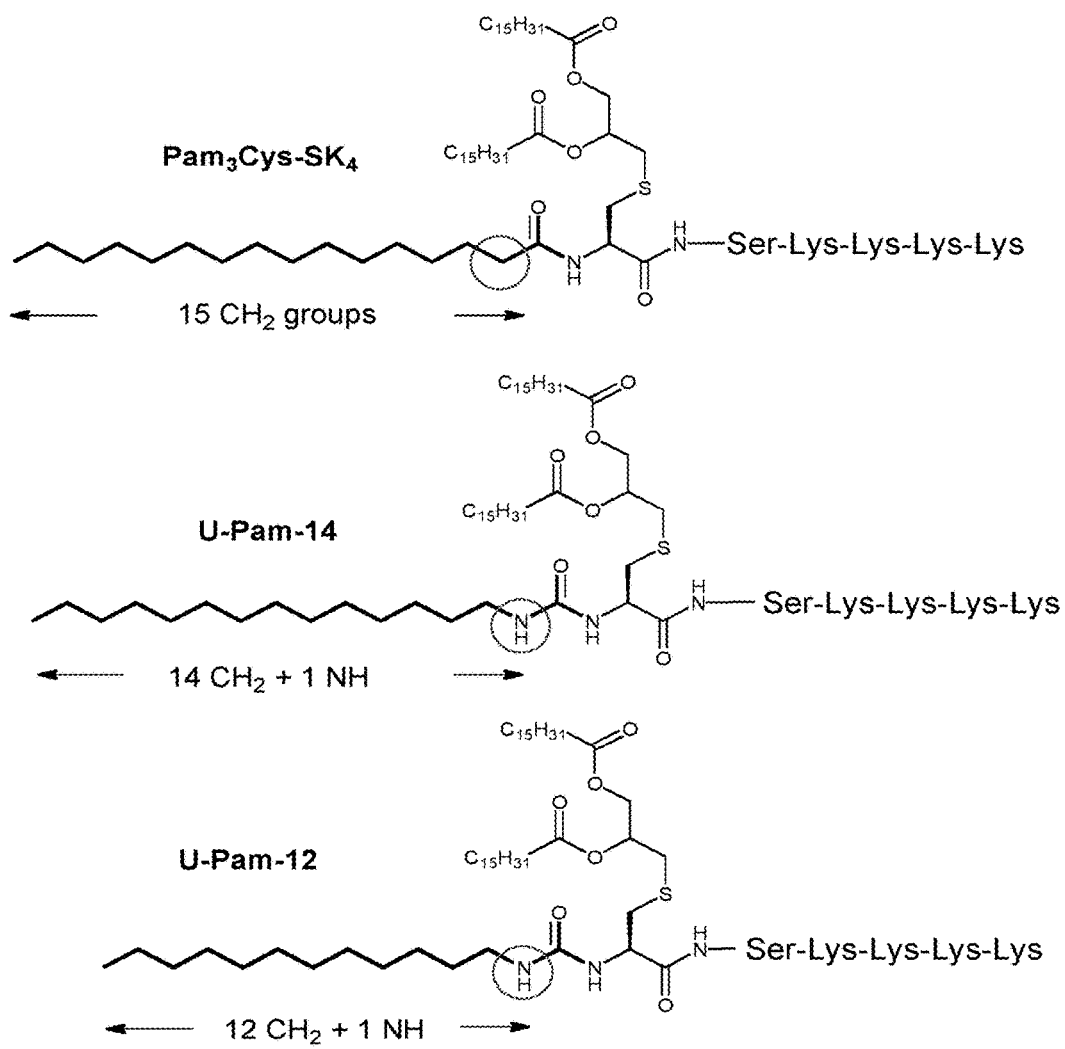
FIG. 1 shows the Pam3Cys-SK4 compound according to the state of the art and two examples of compounds according to the present invention.

The compound (1) according to the present invention may have group X which is S or O. The naturally occurring O is preferred for synthetic ease. The S atom is a well known variant for the skilled person. Y is sulphur or selene and preferably sulphur as illustrated in the examples.

$R^1$ and $R^2$ are each independently a branched or straight group having up to 17 atoms selected from carbon, nitrogen, oxygen and sulphur, preferably straight alkyl groups having up to 17 carbon atoms, preferably 10 to 17 carbon atoms. In an embodiment, $R^1$ and $R^2$ are preferably each independently branched or straight aliphatic groups having up to 17 atoms (i.e. each 1, 2, 3, 4, 5, 6, 7, 8, 9, 10, 11, 12, 13, 14, 15, 16, or 17 atoms) in length containing one or more selected from carbon, nitrogen, oxygen and sulphur. The person skilled in the art knows that the term "up to 17 atoms in length" means in the context of the invention that the backbone of the branched or straight group comprises up to 17 atoms; thus the hydrogen atoms of an aliphatic group are not included in calculating the number of up to 17 atoms. A further preferred group $R^1$ and $R^2$ is a straight chain alkyl group with 15 carbon atoms. Groups with fewer carbon atoms, resulting in a less lipophilic version of the compound, may be advantageous because these may have better solubility properties and therefore exhibit more predictable behaviour in solution.

In formula (1) n is 0 to and including 18, preferably at least 4 and more preferably from 11 to and including 15. Applicants found positive results for compounds wherein n is 11 and wherein n is 13.

In a first embodiment, R is an organic group comprising one or more peptides. In this respect, the compound according to the invention is referred to as a peptide-conjugate. These peptides may contain only natural amino acids, but also synthetic amino acids may be comprised in these peptides. Preferably, R is a peptide of up to 60 amino acids. Examples of suitable peptides are SSNASK4, SR8, RPDRY-NH$_2$ and QPDRY-NH$_2$. A preferred peptide is SK$_m$, wherein m is 1, 2, 3, 4 or 5. Preferably m is 4. The SK4 is also known as SerLysLysLysLys. The S part of the SK$_m$ peptide and more preferably the S part of the SK4 peptide may suitably be modified as described below and the SK$_m$ peptide may optionally be further coupled to an antigen. The preferred modified SK$_m$ peptide is presented by:

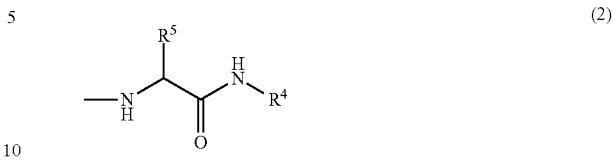

(2)

in which $R^4$ represents the K$_m$ peptide part, optionally further coupled to an antigen, and $R^5$ is hydrogen or a relatively small group comprising one to six atoms chosen from carbon, nitrogen and/or oxygen. m is preferably 4. Examples of possible groups $R^5$ are hydrogen, C1-C6 alkyl, preferably a C1-C4 alkyl, C2-C6 alkenyl, preferably a C2-C3 alkenyl, C2-C6 alkynyl, preferably a C2-C3 alkynyl, C1-C5 hydroxyalkyl, C1-C5 mercaptoalkyl, C1-C5 aminoalkyl, C1-C4-cyanoalkyl, C1-C3-azidooalkyl, for example a —CH$_2$N$_3$ group, C1-C6-haloalkyl, for example —CH$_2$X group (X=F, Cl, Br), aromatic 5 or 6-membered rings containing one or more selected from carbon, nitrogen, oxygen and sulphur, and 3- to 6-membered (hetero)cyclic rings containing one or more selected from carbon, nitrogen, oxygen and sulphur. $R^5$ is preferably hydrogen, a —CH$_2$—OH group, —CH$_2$—CH$_3$ group, —(CH$_2$)$_2$—CH$_3$ group, —(CH$_2$)$_3$—CH$_3$ group, —CH$_2$C≡CH group, —CH$_2$CH=CH$_2$, —(CH$_2$)$_2$NH$_2$ group, —CH$_2$—SH group, —CH$_2$-2-thiophene group, 2-thiophene group or a —CH$_2$—CN group, and more preferably $R^5$ is a —CH$_2$—OH group, —CH$_2$—CH$_3$ group, —(CH$_2$)$_2$—CH$_3$ group, —(CH$_2$)$_3$—CH$_3$ group, —CH$_2$C≡CH group, —CH$_2$CH=CH$_2$ or a —(CH$_2$)$_2$NH$_2$ group. The configuration of the asymmetric carbon to which $R^5$ is attached can be L or D, and preferably the configuration is L.

Group R may comprise an antigen and more preferably group $R^4$ in formula (2) comprises an antigen. The antigen may be coupled to the peptide, in particular to the K$_m$ peptide part, either directly or via a spacer molecule: a linker. A "linker" in the context of the invention is understood to mean a low molecular weight moiety with at least two attachment points for moieties. In this respect, a divalent linker has two such attachment points and a multivalent linker has at least three such attachment points. Via one of these attachment points, the linker is attached to the peptide moiety of R, and each of the one or more remaining attachment points are/is attached to a antigen as defined above. These attachment points originate from functional groups in the precursor of the linker and allow at least one antigen to be attached to the adjuvant compound according to the invention. A linker preferably has a molecular weight of at most 800 Da. This is all conventional chemistry.

Examples of suitable chemical linkages in which the antigen is attached to the linker and/or in which the linker is attached to the R-group of the adjuvant compound according to the invention are organic molecules containing an aliphatic chain and optionally including single or repetitive thioether, amide, amine, oxime, disulfide, thiazolidine, thiourea, ester, thioester, ether, carbamate, thiocarbamate, carbonate, thiocarbonate, hydrazone, sulfate, sulfamidate, sulfone, sulfonamide, phosphate, phosphorothioate, glyoxylic-oxime, or a bond obtained via Diels-Alder cycloaddition, Staudinger ligation, native ligation or Huisgen 1,3-dipolar cycloaddition. Methods of coupling are i.a. described in Chem. Soc. Rev. 2010, 39, 2054, which is incorporated herein by reference.

Examples of suitable linkers are Unylinker-type linkers, α,ω-dihydroxyalkanes, and oligo- or polyethyleneglycol derivatives. The linker may include natural and non-natural amino acid residues, alicyclic compounds such as cyclohexane and cyclopentane derivatives and (hetero) aromatic rings, such as substituted phenyl and substituted triazole.

When no linker is used, the antigen is coupled to directly to the remainder of the compound according to the invention, preferably to the Km peptide part of group R. Examples of suitable bonds between the Km peptide part and the antigen are thioether, disulphide, amide or ester bonds.

Instead of the covalent incorporation of the antigen in the adjuvant compound according to the invention, optionally via a linker, the coupling may also occur via an ionic bond. An example of a suitable ionic bond is the coulombic interaction between a positively charged amine group of a lysine side chain in the Km peptide part and a negatively charged amino acid residue of the antigen. In further embodiments, the adjuvant compound according to the invention, preferably the compound according to formula (1), may be coupled to an antigen but may also be coupled to another compound, using the techniques described herein, such an antibody, a nucleic acid such as a polynucleotide and an oligonucleotide. The other compound may preferably be coupled to the group R and more preferably to group $R^4$ in formula (2). The other compound may be coupled to the peptide in formula (2), in particular to the $K_m$ peptide part.

In a second embodiment, R is an organic group comprising one or more nucleic acids, such as one or more oligonucleotides or one or more polynucleotides, preferably one or more oligonucleotides. An oligonucleotide may be a sense or an antisense oligonucleotide. In this respect, the compound according to the invention is referred to as a nucleic acid-conjugate. Such a nucleic acid may be directly coupled to the compound of formula (1), or via a linker. When no linker is used, the nucleic acid is preferably coupled via an oxygen atom or a phosphorus atom of the phosphodiester group at the 3'-terminus or the 5'-terminus of the nucleic acid to the compound according to formula (1), via the carbonyl carbon atom to which R is attached. Preferably, a linker as described above is used. One end of such a linker is attached to the compound according to formula (1) via the carbonyl carbon atom to which R is attached, and the other end of the linker is attached to the nucleic acid, preferably via an oxygen atom or a phosphorus atom of the phosphodiester group at the 3'-terminus or the 5'-terminus of the oligonucleotide.

In the context of this invention, a "nucleic acid" preferably has a length of 5 to 60 nucleotides (i.e. 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides). A nucleic acid such as a polynucleotide and an oligonucleotide may be any nucleic acid known to the person skilled in the art, such as a DNA, RNA, PNA or combinations thereof. Thus, a nucleic acid may comprise naturally occurring nucleotides, or nucleotides analogues, which have one or more modifications with respect to naturally occurring nucleotides. In this respect, naturally occurring nucleotides are those which are comprised in DNA or RNA. Nucleotides analogues comprise at least one modification selected from a modified nucleobase, a modified sugar moiety, a modified internucleoside linkage, and combinations thereof. Exemplary of modifications is a modified backbone, comprising a modified sugar moiety and/or a modified internucleoside linkage. Thus, the backbone and nucleobases of the nucleic acid may be modified according to techniques commonly known to the person skilled in the art, in order to enhance or reduce specificity and/or to enhance or decrease stability. Accordingly, a nucleic acid may contain a RNA residue, a DNA residue, a nucleotide analogue or equivalent as will be further detailed herein below.

It is preferred that a nucleic acid comprises a or at least one residue that is modified to increase nuclease resistance, and/or to increase the affinity of an (antisense) nucleotide for a target sequence. Therefore, in a preferred embodiment, a nucleic acid comprises a or at least one nucleotide analogue or equivalent, wherein a nucleotide analogue or equivalent is defined as a residue having a modified base, and/or a modified backbone, and/or a non-natural internucleoside linkage, or a combination of these modifications.

In a preferred embodiment, a nucleotide analogue or equivalent comprises a modified backbone. Examples of such backbones are provided by morpholino backbones, carbamate backbones, siloxane backbones, sulfide, sulfoxide and sulfone backbones, formacetyl and thioformacetyl backbones, methyleneformacetyl backbones, riboacetyl backbones, alkene containing backbones, sulfamate, sulfonate and sulfonamide backbones, methyleneimino and methylenehydrazino backbones, and amide backbones. Phosphorodiamidate morpholino oligomers are modified backbone oligonucleotides that have previously been investigated as antisense agents. Morpholino oligonucleotides have an uncharged backbone in which the deoxyribose sugar of DNA is replaced by a six membered ring and the phosphodiester linkage is replaced by a phosphorodiamidate linkage. Morpholino oligonucleotides are resistant to enzymatic degradation and appear to function as antisense agents by arresting translation or interfering with pre-mRNA splicing rather than by activating RNase H. Morpholino oligonucleotides have been successfully delivered to tissue culture cells by methods that physically disrupt the cell membrane, and one study comparing several of these methods found that scrape loading was the most efficient method of delivery; however, because the morpholino backbone is uncharged, cationic lipids are not effective mediators of morpholino oligonucleotide uptake in cells.

It is further preferred that the linkage between a residue in a backbone does not include a phosphorus atom, such as a linkage that is formed by short chain alkyl or cycloalkyl internucleoside linkages, mixed heteroatom and alkyl or cycloalkyl internucleoside linkages, or one or more short chain heteroatomic or heterocyclic internucleoside linkages.

A preferred nucleotide analogue or equivalent comprises a Peptide Nucleic Acid (PNA), having a modified polyamide backbone (Nielsen, et al. (1991) Science 254, 1497-1500). PNA-based molecules are true mimics of DNA molecules in terms of base-pair recognition. The backbone of the PNA is composed of N-(2-aminoethyl)-glycine units linked by peptide bonds, wherein the nucleobases are linked to the backbone by methylene carbonyl bonds. An alternative backbone comprises a one-carbon extended pyrrolidine PNA monomer (Govindaraju and Kumar (2005) Chem. Commun, 495-497). Since the backbone of a PNA molecule contains no charged phosphate groups, PNA-RNA hybrids are usually more stable than RNA-RNA or RNA-DNA hybrids, respectively (Egholm et al (1993) Nature 365, 566-568).

A further preferred backbone comprises a morpholino nucleotide analog or equivalent, in which the ribose or deoxyribose sugar is replaced by a 6-membered morpholino ring. A most preferred nucleotide analog or equivalent comprises a phosphorodiamidate morpholino oligomer (PMO), in which the ribose or deoxyribose sugar is replaced by a 6-membered morpholino ring, and the anionic phosphodiester linkage between adjacent morpholino rings is replaced by a non-ionic phosphorodiamidate linkage.

In yet a further embodiment, a nucleotide analogue or equivalent of the invention comprises a substitution of at least one of the non-bridging oxygens in the phosphodiester linkage. This modification slightly destabilizes base-pairing but adds significant resistance to nuclease degradation. A preferred nucleotide analogue or equivalent comprises phosphorothioate, chiral phosphorothioate, phosphorodithioate, phosphotriester, aminoalkylphosphotriester, H-phosphonate, methyl and other alkyl phosphonate including 3'-alkylene phosphonate, 5'-alkylene phosphonate and chiral phosphonate, phosphinate, phosphoramidate including 3'-amino phosphoramidate and aminoalkylphosphoramidate, thionophosphoramidate, thionoalkylphosphonate, thionoalkylphosphotriester, selenophosphate or boranophosphate.

A further preferred nucleotide analogue or equivalent of the invention comprises one or more sugar moieties that are mono- or disubstituted at the 2', 3' and/or 5' position such as a —OH; —F; substituted or unsubstituted, linear or branched lower (C1-C10) alkyl, alkenyl, alkynyl, alkaryl, allyl, aryl, or aralkyl, that may be interrupted by one or more heteroatoms; O—, S—, or N-alkyl; O—, S—, or N-alkenyl; O—, S— or N-alkynyl; O—, S—, or N-allyl; O-alkyl-O-alkyl, -methoxy, -aminopropoxy; aminoxy, methoxyethoxy; -dimethylaminooxyethoxy; and -dimethylaminoethoxyethoxy. The sugar moiety can be a pyranose or derivative thereof, or a deoxypyranose or derivative thereof, preferably a ribose or a derivative thereof, or deoxyribose or derivative thereof. Such preferred derivatized sugar moieties comprise Locked Nucleic Acid (LNA), in which the 2'-carbon atom is linked to the 3' or 4' carbon atom of the sugar ring thereby forming a bicyclic sugar moiety. A preferred LNA comprises 2'-O,4'-C-ethylene-bridged nucleic acid (Morita et al. 2001. Nucleic Acid Res Supplement No. 1: 241-242). These substitutions render the nucleotide analogue or equivalent RNase H and nuclease resistant and increase the affinity for the target RNA.

It is understood by a skilled person that it is not necessary for all positions in an (antisense) oligonucleotide to be modified uniformly. In addition, more than one of the aforementioned analogues or equivalents may be incorporated in a single (antisense) oligonucleotide or even at a single position within an (antisense) oligonucleotide. In certain embodiments, an (antisense) oligonucleotide of the invention has at least two different types of analogues or equivalents. In a preferred embodiment, the modification occurs over the full length of the oligonucleotide.

A preferred oligonucleotide is an immunomodulating oligonucleotide that may occur naturally or be a synthetic oligonucleotide. Preferably, such oligonucleotide immunimodulates by acting on a Toll-like receptor, preferably Toll-like receptor 9 (TLR9). Preferably, such oligonucleotide comprises one or more, such as 1, 2, 3, 4, 5, 6, 7 or more, CpG (unmethylated cytidine-phosphate-guanosine (CpG) dinucleotides), more preferably one or more, class B CpG. A preferred class B CpG comprising oligonucleotide is CpG 7909 with the sequence 5'-TCGTCGTTTT-GTCGTTTTGTCGTT-3' (SEQ ID NO: 10) such as described in Drugs R D. 2006;7(5):312-6, which is herein incorporated by reference. Class B CpG comprising oligonucleotides are strong stimulators of human B cell and monocyte maturation. A preferred class B CpG oligonucleotide comprises one or more, preferably three, of the 6mer CpG motif 5'-Pu Py C G Py Pu-3', a partly or fully phosphorothioated backbone, and is preferably 18 to 28 nucleotides, such as 18, 19, 20, 21, 22, 23, 24, 25, 26, 27 or 28 nucleotides, in length. Another preferred CpG comprising oligonucleotide comprises one or more, such as 1, 2, 3, 4, 5, 6, 7 or more, class A CpG. Class A CpG stimulate the production of large amounts of Type I interferons, especially IFNα, induce the maturation of pDCs, and/or are strong activators of NK cells through indirect cytokine signaling. A preferred class A CpG oligonucleotide comprises one or more of a poly G sequence at the 5' end, the 3' end, or both, an internal palindrome sequence, one or more GC dinucleotides within the internal palindrome, and a partially phosphorothioated backbone, preferably 7 to 10 phosphorothioated bases at one or both ends.

In a preferred embodiment, R is organic group comprising a peptide and a nucleic acid, preferably a peptide and an oligonucleotide as described above. In this third aspect of the invention, the compound according to the invention is referred to as a peptide/nucleic acid-conjugate, preferable a peptide/oligonucleotide-conjugate. In this respect, the nucleic acid is coupled to the peptide, either directly or via a linker as described herein, which is in turn coupled to the compound according to formula (1). In a preferred embodiment, the nucleic acid is coupled to $R^4$ or $R^5$, preferably to $R^4$ of the (modified) $SK_m$ peptide represented by formula (2), either directly or via a linker as described herein. Alternatively, the nucleic acid may be coupled to the $K_m$ part of the $SK_m$ peptide, preferably the $SK_4$ peptide, either directly or via a linker as described herein.

In an especially preferred embodiment, the nucleic acid is coupled to the terminal lysine residue of the $SK_m$ peptide, preferably the $SK_4$ peptide, either directly or via a linker as described herein. In this respect, the linker is preferably a linker containing six carbon atoms.

The preparation of peptide/nucleic acid-conjugates is well-known in the art, for example from Carter and LeBean, *J. Nucleic Acids,* 2011 (doi:10.4061/2011/926595), which is incorporated by reference in its entirety.

In a fourth embodiment, R is organic group comprising one or more antibodies. In this respect, the compound according to the invention is referred to as a antibody-conjugate. The antibody may be any antibody known to the person skilled in the art. Preferred antibodies are selected from the list consisting of 1) antibodies directed against specific target molecules on the surface of cancer cells: differentiation antigens such as CD19, CD20, CD30, overexpressed antigens such as HER-2/Neu, epidermal growth factor receptor (EGFR); 2) antibodies directed against surface molecules of T cells such as IL-2 receptor, IL-7 receptor, IL-15 receptor with the aim to delete a subset of T cells causing autoimmune disease or involved in immunoregulation such as non-activated regulatory T cells.

The antibody may be coupled to the compound according to formula (1) as described above for nucleic acids. As such, the antibody may be coupled directly or via a linker as described herein.

Alternatively, the antibody may be coupled to a peptide-conjugate as described above, preferably to $R^4$ of the (modified) $SK_m$ peptide represented by formula (2), either directly or via a linker as described herein. In such a fifth embodiment, R is organic group comprising a peptide and an antibody. In this respect, the compound according to the invention is referred to as a peptide/antibody-conjugate. In this respect, the antibody is coupled to the peptide, either directly or via a linker as described herein, which is in turn coupled to the compound according to formula (1). In a preferred embodiment, the antibody is coupled to $R^4$ or $R^5$, preferably to $R^4$ of the (modified) $SK_m$ peptide represented by formula (2), either directly or via a linker as described herein. Alternatively, the antibody may be coupled to the $K_m$ part of the $SK_m$ peptide, preferably the $SK_4$ peptide, either directly or via a linker as described herein.

In an especially preferred embodiment, the antibody is coupled to the terminal lysine residue of the $SK_m$ peptide, preferably the $SK_4$ peptide, either directly or via a linker as described herein. In this respect, the linker is preferably a linker containing six carbon atoms.

In a sixth embodiment, R is hydroxyl or OH. The compound according to this aspect may be used in combination with peptides, nucleic acids or antibodies for the applications as described below, such as for co-administration.

Preferred compounds according to the invention are represented by formula (1), wherein $R^1$ and $R^2$ are each independently branched or straight groups having up to 17 atoms selected from carbon, nitrogen, oxygen and sulphur, n is 0 to and including 18, X is S or O and R is an organic group comprising one or more peptides, one or more nucleic acids, one or more antibodies or combinations thereof. In other words, preferred compounds according to the invention are the peptide-conjugates, the nucleic acid-conjugates, the peptide/nucleic acid-conjugates, the antibody-conjugates or the peptide/antibody-conjugates as described above. Especially preferred are the peptide-conjugates, the peptide/nucleic acid-conjugates or the peptide/antibody-conjugates as described above. Accordingly, it is especially preferred that R is an organic group comprising one or more peptides, and optionally one or more nucleic acids or one or more antibodies.

The compound according to the invention may be a mixture of R- and S-epimers or suitably the R-epimer at the C-2 of the 2-(OC(O)R2)-3-(OC(O)R1)propyl group.

The invention is also directed to a process to prepare the novel compounds by standard solid phase peptide synthesis protocol, comprising the steps:
  (a) providing R-H, which is optionally immobilized and/or side-chain protected;
  (b) coupling of the substituted cysteine building block Fmoc-(S-(2-(OC(O)R²)-3-(OC(O)R¹))propyl)-Cys-OH to R-H;
  (c) cleavage of the Fmoc-group from the N-terminus; and
  (d) treatment of the resulting peptide with alkylisocyanate or alkylisothiocyanate H—$(CH_2)_n$—N=C=X.

In this process, R, $R^1$, $R^2$, X and n are defined as described above. Preferably, the substituted cysteine building block is Fmoc-Pam$_2$-Cys-OH, thus with $R^1$ and $R^2$ being straight alkyl groups having 15 carbon atoms. In a preferred embodiment, the process is for preparing the peptide-conjugates according to the invention and involves the following steps:
  (a) Solid-phase peptide synthesis, thereby obtaining an immobilized and side-chain protected peptide R-H,
  (b) coupling of Fmoc-(S-(2-(OC(O)R²)-3-(OC(O)R¹))propyl)-Cys-OH, preferably Fmoc-Pam$_2$-Cys-OH with the immobilized and side-chain protected peptide R-H obtained in step (a),
  (c) cleavage of the N-terminal Fmoc-group from the Pam$_2$Cys-moiety
  (d) reacting Fmoc-liberated product of step (c) with an alkylisocyanate or alkylisothiocyanate H—$(CH_2)_n$—N=C=X, preferably alkylisocyanate H—$(CH_2)_n$—N=C=O,
  (e) performing an acid-mediated deprotection and cleavage from the solid phase of the product of step (d), and
  (f) performing a RP HPLC purification.

Figure 2:
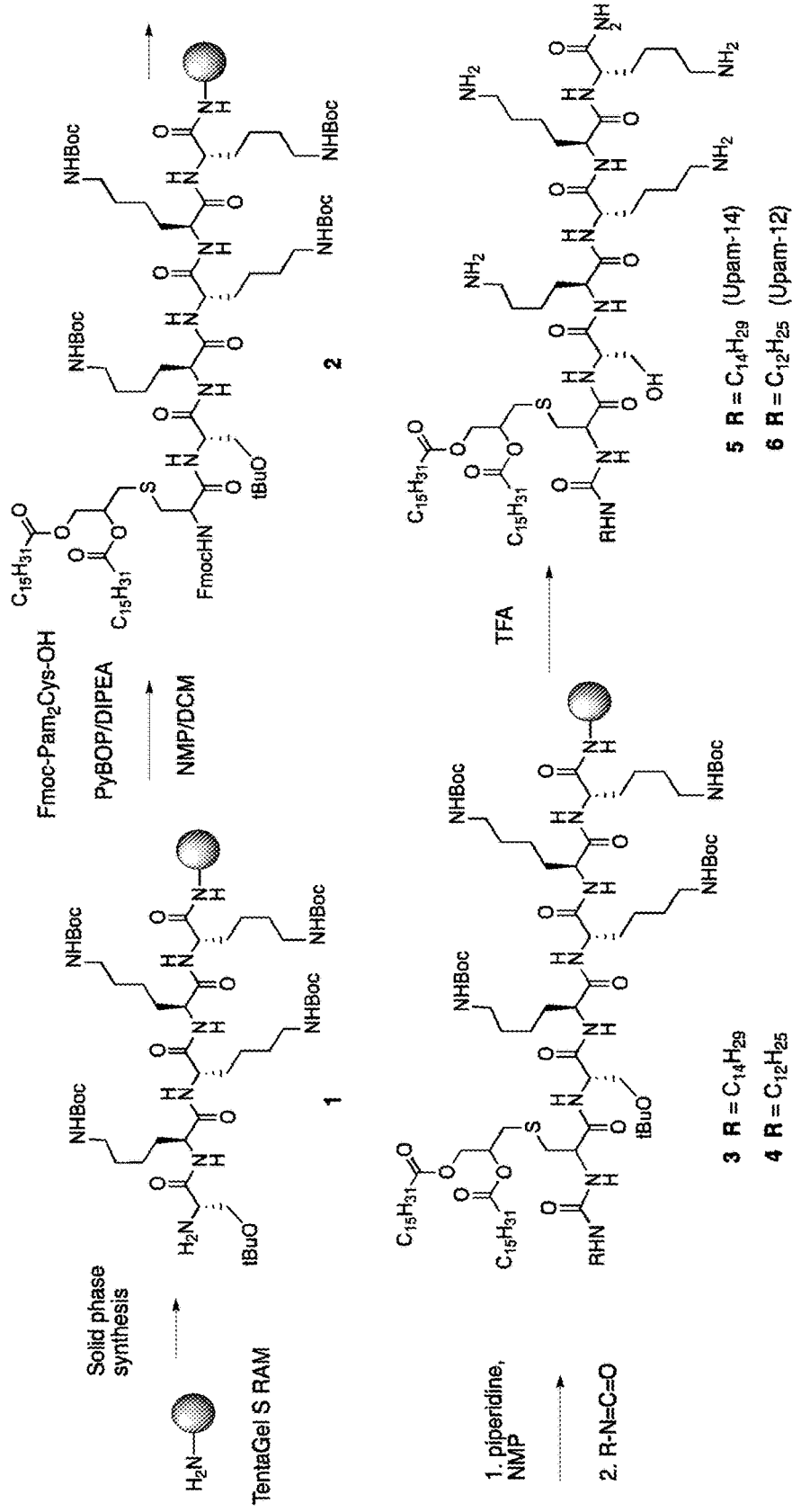
FIG. 2 shows a synthesis scheme for the preparation of a compound according to the present invention.

The above process is illustrated by FIG. 2 and below for the synthesis of U-Pam-14 and U-Pam-12. FIG. 2 describes the solid-phase synthesis of target compounds U-Pam-14 and U-Pam-12, wherein the following terms are defined as:

TentaGel S RAM is functionalized copolymer of polystyrene and polyethylene glycole provided with Rink-amide linker (a common solid phase for peptide synthesis)

NHBoc is tert-butyloxycarbonyl protected amino group tBu is tert-butyl

Fmoc-Pam$_2$Cys-OH is Fluorenylmethyloxycarbonyl-S-[2,3-bis(palmitoyloxy)propyl]-L-cysteine.

PyBOP, is (benzotriazol-1-yl-oxytripyrrolidinophosphonium hexafluorophosphate; a phosphonium activating reagent commonly used in peptide chemistry DIPEA is diisopropylethylamine, an organic base commonly used in peptide chemistry TFA is trifluoroacetic acid NMP is N-methylpirrolidone, a solvent DCM is dichloromethane, a solvent The solid-phase peptide synthesis of step (a) is known and for example described in Dick, F. Peptide Synthesis Protocols. In: M. W. Pennington and B. M. Dunn (eds.) Methods in Molecular Biology, Vol. 35, pp. 63-72. Totowa: Humana Press Inc., 1994, which is hereby incorporated by reference. In step (a) immobilized and side chain protected peptide 1 is assembled starting from TentaGel S resin equipped with Rink amide linker (Tentagel S RAM in Scheme 1). The synthesis as illustrated is suitably performed in a fully automated fashion on ABI 433A peptide synthesizer applying Fmoc/OtBu chemistry with HCTU as the coupling reagent and DIPEA as the base. It should be understood that other peptide synthesizers known in the art may also be used. Upon the final Fmoc-cleavage using for example a 20% piperidine in NMP the peptide resin (1) is suitably removed from the instrument, washed with DCM and dried. In step (b) the Fmoc-Pam$_2$Cys-OH is suitably coupled manually to the peptide resin 1 to give fully protected peptide resin 2. Phosphonium coupling reagent PyBOP is used in this coupling step and the base (DIPEA) is suitably added in two portions to prevent base-catalyzed side reactions. After piperidine-mediated cleavage of Fmoc-group in step (c), the resin is suitably washed with NMP and the resulting immobilized N-lipohexapeptide with free N-terminal amino group was treated in step (d) with tetradecyl isocyanate in DCM/NMP mixture overnight to give immobilized and fully protected UPam-14 (3). The product was cleaved in step (e) from the resin with concomitant removal of the side chain protecting groups by acidolysis with suitably 95% TFA in the presence of $H_2O$ and TIS as cation scavengers. Subsequent in step (f) RP HPLC purification on $O_4$ phase and lyophylization furnished pure UPam-14 (5) as a white solid. The same protocol starting from resin 2 may be employed for the preparation of UPam-12 (6) except that dodecyl isocyanate is used instead of tetradecyl isocyanate on the stage of the introduction of urea connected N-terminal lipophilic chain to immobilized lipohexapeptide.

The above-described synthesis for the peptide-conjugate may be adapted to provide the other conjugates according to the invention, as known in the art. As such, the peptide R-H may be replaced by R-H, wherein R is an organic group comprising one or more nucleic acids, one or more antibodies or combinations thereof with peptides. In another embodiment, the peptide-conjugates are prepared as described above, and are subsequently conjugated with one or more nucleic acids or one or more antibodies, as such obtaining peptide/nucleic acid-conjugates or peptide/antibody-conjugates. Such conjugation methods are well-known in the art, and are for example described in Carter and LeBean, *J. Nucleic Acids,* 2011 (doi:10.4061/2011/926595), which is incorporated by reference in its entirety.

The compounds according to the invention as described above are suitably used as part of a medicament or vaccine. The invention is thus directed to said compound or a composition comprising a compound according to the invention for use as a medicament, preferably a medicament to treat a disease or condition as defined herein. More preferably the invention is directed to a compound or a composition comprising a compound according to the invention to enhance a TLR2 mediated innate immune reaction in a patient, preferably a mammal, more preferably a human. The compound may be used in a so-called mono-therapy wherein in a stand-alone treatment the existing immune system is stimulated, for example for local administration in the lymphoid drainage area of a tumor. Other standalone applications of the compound according to the invention as described above are the treatment of damage or disease of the central nervous system such as axon regeneration of (optic) nerves preferably by injection into the eye and treatment of ischemia such as ischemia of the heart or brain or other organs preferably by systemic injection. A further standalone application is the treatment of infections such viral, bacterial, fungal, protozoa and parasite infections such as visceral leishmanias and visceral endophtalmitis.

In stand-alone applications, the compound according to the invention may be applied in the form of a solution in liquid form, a suspension or emulsion, a cream, spray, or any other formulation known to the person skilled in the art. For treatment of ischemia and axon regeneration, the compound according to the invention is preferably in a pharmaceutically acceptable injectable formulation.

In an aspect of the invention, a compound according to the invention is used in a method for treatment of a disease or condition as defined herein.

A compound may already comprise an antigen and/or another compound such an antibody, a nucleic acid such as a polynucleotide and an oligonucleotide, as defined herein. Alternatively or in combination with a previous embodiment, a composition comprising a compound as identified herein may further comprise an antigen and/or another compound such an antibody, a nucleic acid such as a polynucleotide and an oligonucleotide, as defined herein as a separate molecule. The invention is therefore also directed to a compound comprising an antigen and/or another compound such an antibody, a nucleic acid such as a polynucleotide and an oligonucleotide, and/or a composition comprising said compound or a composition comprising a compound and an antigen and/or another compound such an antibody, a nucleic acid such as a polynucleotide and an oligonucleotide, as a separate molecule for use as a medicament, preferably as a preventive or therapeutic vaccine composition. In particular, the invention is directed to a vaccine composition comprising the compound according to the invention as an adjuvant and at least one antigen and/or another compound such an antibody, a nucleic acid such as a polynucleotide and an oligonucleotide, wherein the antigen or other compound may be present as a separate compound or coupled to the compound according to the invention as described above. Preferably the antigen or other compound is part of the compound according to the invention, wherein the antigen or other compound is coupled to the adjuvant compound described above. Such a linkage has the advantage that, in use, an enhanced immune response by simultaneous stimulation of antigen presenting cells, in particular dendritic cells, that internalize, metabolize and display antigen is achieved.

Accordingly in an aspect of the invention, there is provided a method for the induction, maintenance and/or enhancement (boost) of an immune response in a subject against an antigen and/or for the prevention, delay and/or treatment of a disease or condition associated with said antigen in a subject wherein a compound or a composition as defined herein is administrated to said subject. Each feature of said method is identified herein.

The antigen may be any material that can induce, maintain or enhance an immune response by the immune system of a subject. A preferred subject is an animal. Preferably an animal is a mammal, preferably a human. It is to be understood that said induced or enhanced immune response is specific for said antigen. An antigen-specific immune response is preferably a T cell response or cellular immune response. Such antigen therefore preferably comprises a T cell epitope: a T helper and/or a CTL epitope.

An antigen can be a full length biomacromolecule or a fragment thereof. The antigen can for example be synthetic material, purified subunits of a protein, a protein fragment, a digest of a protein, a peptide, a DNA molecule, a cDNA molecule, a RNA molecule, an oligonucleotide, an oligosaccharide, a crude composition, preferably of biological origin such as a whole microbe, a bacterial, yeast or fungal lysate, sonicate or fixate or a mixture thereof. In an embodiment, when an antigen is a peptide, said peptide may be from 6 to 60 amino acids, or 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 amino acids or more. In said embodiment, said peptide is therefore distinct from the protein it derives from. An antigen may be a tumor antigen, viral antigen, bacterial antigen or parasite antigen. An antigen may be derived from an infectious agent. Such infectious agent may cause cancer and/or a premalignant condition. Preferably the antigen is a chemically synthesized or enzymatically produced peptide, oligonucleotide or oligosaccharide and more preferably it has been obtained after purification. An antigen may also be in the form of a nucleic acid (DNA, or RNA) encoding said antigen or fragment thereof. The RNA or DNA molecules may be 'naked' DNA, preferably comprised in vesicles or liposomes, or they may be comprised in a vector. The vector may be any (recombinant) DNA or RNA vector known in the art, and preferably is a plasmid; wherein said DNA encoding said antigen is operably linked to regulatory sequences conferring expression and translation of the encoded messengers. The vector may also be any DNA or RNA virus, such as, but not limited to, Adenovirus, Adeno-Associated Virus (AAV), a retrovirus, a lentivirus, modified Vaccinia Ankara virus (MVA) or Fowl Pox virus, or any other viral vector capable of conferring expression of polypeptides into a chosen subject. DNA vectors may be non-integrating, such as episomally replicating vectors, or may be vectors integrating in the host genome by random integration or by homologous recombination.

The antigen is preferably selected as a single or multiple component from the group consisting of a protein of a pathogen, a recombinant protein, a peptide, a hapten, a polysaccharide, a glycoprotein, a lipopolysaccharide, a DNA molecule, a cDNA molecule, an RNA molecule (all polynucleotides), a cancer cell and a micro-organism. A preferred composition comprises a compound according to the invention as adjuvant and at least one viral antigen or bacterial antigen, for example TBC; tetanus and *Helicobacter Pylori*, or parasite antigen or tumor antigen suitable for treating or preventing viral or parasitic or bacterial infections or treating or preventing cancer or comprises a compound according to the invention, wherein group R comprises a viral antigen or bacterial antigen, for example TBC and tetanus, or parasite antigen or tumor antigen suitable for treating or preventing viral or parasitic or bacterial infection or treating or preventing cancer.

Suitable viral antigens are influenza virus antigen, such as for example HA: haemaglutinin or neuraminidase antigen; human papilloma virus (HPV) antigen, such as E2, E6, E7; human immunodeficiency virus (HIV) antigen, such as for example GP120, GP140, GP160, vesicular stomatitis virus antigen, for example vesicular stomatitis virus glycoprotein; cytomegalovirus (CMV) antigen; hepatitis virus antigens, such as for example hepatitis A(HAV), B(HBV), C(HCV), D(HDV) and G(HGV): L-HBsAg, S-HBsAg, M-HBsAg, pre 5, respiratory syntytial virus (RSV) antigen; SV40 virus antigen, such as Large T, small T; EBV antigen, such as EBNA, Kaposi Sarcoma Virus (KSV) antigen, Human T-Lymphotropic Virus-1(HTLV-1) antigen, Merkel cell virus (MCV) antigen or herpes simplex virus antigen.

The HPV strains from which the antigen or peptide used derived is preferably a high risk HPV serotype, such as serotypes 16, 18, 31, 33 or 45, more preferably from the serotype 16, 18, 31 or 33, most preferably from serotype 16 or 18, of which 16 is most preferred. The amino acid sequence of the HPV serotype 16 E2, E6 and E7 proteins are depicted in SEQ ID NO 1-3 respectively. The amino acid sequence of the HPV serotype 18 E2, E6 and E7 proteins are depicted in SEQ ID NO 4-6, respectively.

Suitable parasite antigens may be derived from protozoa, nematoda, trematoda or cestoda, such as *Cryptosporidium hominis* or *parvum*, *Schistosoma haematobium, mansoni* or *japonicum*; *Plasmodium falciparum, malariae, vivax* or *ovale*; *Leishmania major, tropica, aethiopica, mexicana, donovani, infantum* or *braziliensis*; *Toxoplasma Gondii*.

Suitable bacterial antigens may be antigens derived from *Mycobacterium Tuberculosis, Streptococcus pneumoniae, Staphylococcus Aureus, Vibrio cholera, Neisseria meningitides*.

Tumor antigens are antigens expressed on tumor cells. This group of antigens is preferably said to be associated with cancer in the following illustrating and non-limitative cases: antigens derived from proteins that are expressed solely on tumors and not or only in a limited amount on normal adult cells, antigens derived from proteins that are over-expressed on tumors as compared to normal adult cells, antigens derived from proteins that have been mutated in tumors, antigens that are aberrantly expressed in a given tissue of cancer patients by comparison with the corresponding tissue of a subject not having cancer. An aberrantly expressed antigen may be de novo expressed in a tissue wherein it is normally not expressed. A mutated antigen may be a splice variant. A mutated antigen may further be produced as an aberrant fusion protein as a result of a translocation. Examples of antigens that are known to be associated with cancer are p53, MDM-2, HDM2 and other proteins playing a role in p53 pathway, molecules such as survivin, telomerase, cytochrome P450 isoform 1 B1, Her-2/neu, and CD19 and all so-called house hold proteins.

Suitable antigens include antigens derived from infectious agents that cause diseases such as cancers and/or premalignant conditions. Examples of such infectious agents are HPV, which causes diseases such as genital warts, a cervical cancer, head and neck cancer, Penile cancer, Vulva cancer, Anal cancer, nasopharyngeal cancer, CIN, VIN, PIN, VAIN and AIN, HCV and HBV, which are involved in liver carcinoma, SV40, which is involved in mesothelioma, HTLV-1, which is involved with T cell leukemia/lymphoma, Merkel cell virus, which is involved with Merkel cell carcinoma and KSV, which is involved with Kaposi sarcoma.

The above vaccine compositions may be used as a preventive (i.e. prophylactic) or therapeutic (i.e. curative) vaccine composition for both acute or persistent infections or disease caused thereby.

The vaccine composition is also preferably used as a preventive or therapeutic vaccine composition designed to elicit specific immune responses against a given disease or condition wherein said antigen is associated or linked with. A preferred disease or condition is a cancer. A cancer may be a non-viral cancer or a viral cancer such as a cancer induced by HPV. A preferred vaccine composition comprises a compound according to the invention as adjuvant and at least one non viral cancer-associated tumor antigen or comprises a compound according to the invention, wherein group R comprises a non viral cancer-associated tumor antigen. The cancer to be treated or be prevented may be a brain cancer, renal cell carcinoma, a melanoma, a leukemia, a lung cancer, a stomach cancer, an esophageal cancer, a thyroid cancer, a pancreatic cancer, a breast cancer, a prostate cancer, an ovarian cancer, a uterine cancer, a testicular cancer, a cholangioma, a liver cancer, a colon cancer, a gastrointestinal cancer, a bladder cancer, or a rectal cancer. In addition pre-malignant lesions may be treated or prevented by use of the vaccine composition. Pre-malignant lesions are lesions that have undergone genetic changes that predispose cells to become cancer cells. These pre-malignant lesions may evolve into cancers over time. Examples of suitable tumor antigens are gp100, MART-1, MAGE-1, BAGE, GAGE, HAGE, tyrosinase, CEA (cancer embryonic antigen), p53, PSA (prostate specific antigen), PSMA (prostate specific membrane antigen); PRAME, HER2/neu, MAGE-1, MAGE-2, MAGE-3, NY-ESO-1, MUC-1, SART-1 or SART-3, XAGE-1 B, Tyrosinase, TERT (telomerase reverse transcriptase), WT1, Survivin-2B, gp75, MDM2, telomerase, al[rho]h-1 fetoprotein, CA125, CA15-3, CA19-9, G250, HER2, BCR-ABL, Ras, PML-RARa, PR1, SSX-2, HSP70 or a peptide analogue derived from any of the above mentioned viral, non-viral, tumor, bacterial or parasite antigens.

A preferred antigen comprises a peptide comprising a T cell epitope, i.e. a CD4 and/or CD8 T cell epitopes that are derived from any of the abovementioned viral, non-viral, tumor, bacterial or parasite antigens, but preferably from the high risk human papilloma virus (HPV)-specific E6 and E7 oncoproteins as described in WO02/070006 and WO2008/147187, which publications are hereby incorporated by reference.

A preferred peptide originating from HPV serotype 16 E6 as identified above by SEQ ID NO: 2 is selected from the group consisting of a peptide comprising or consisting of or overlapping with:

E6 1-32, E6 19-50, E6 41-65, E6 55-80, E6 71-95, E6 85-109, E6 91-122, E6 109-140 and E6 127-158.

A preferred peptide originating from HPV serotype 16 E7 as identified above by SEQ ID NO: 3 is selected from the group consisting of a peptide comprising or consisting of or overlapping with:

E7 1-35, E7 22-56, E7 43-77 and E7 64-98.

A preferred peptide originating from HPV serotype 16 E6 or E7 as identified above by SEQ ID NO: 2 or 3 is selected from the group consisting of a peptide comprising or consisting of or overlapping with:

E6 1-32, E6 19-50, E6 41-65, E6 55-80, E6 71-95, E6 85-109, E6 91-122, E6 109-140, E6 127-158, E7 1-35, E7 22-56, E7 43-77 and E7 64-98. The invention also encompasses a peptide originating from HPV as identified in these preceding paragraphs and comprising 1, 2, 3, 4, 5, 6, 7, 8, 9 or more additional amino acids in total derived from the corresponding positions of the corresponding E6 or E7 HPV protein. These additional amino acids may be present at the N and/or at the C terminal of said peptide. However, such peptides are preferably distinct from a full length E6 or E7 protein.

In another embodiment, a peptide originating from HPV has a length of 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids and preferably comprises the contiguous amino acid sequence comprising an epitope that is selected from the group consisting of amino acids 11-32 of an HPV E6 protein, amino acids 13-22 of an HPV E6 protein amino acids, amino acids 29-38 of an HPV E6 protein, 37-68 of an HPV E6 protein, amino acids 52-61 of an HPV E6 protein, amino acids 51-72 of an HPV6 protein, amino acids 55-86 of an HPV E6 protein, amino acids 61-82 of an HPV E6 protein, amino acids 71-92 of an HPV E6 protein, amino acids 73-105 of an HPV E6 protein, amino acids 91-112 of an HPV E6 protein, amino acids 101-122 of an HPV E6 protein, amino acids 121-142 of an HPV E6 protein, amino acids 129-138 of an HPV E6 protein, amino acids 137-146 of an HPV E6 protein, amino acids 149-158 of an HPV E6 protein amino acids 1-32 of an HPV E7 protein, amino acids 11-19 of an HPV E7 protein, amino acids 21-42 of an HPV E7 protein, amino acids 51-72 of an HPV E7 protein, amino acids 76-86 of an HPV E7 protein; amino acids 13-22 of an HPV E6 protein, amino acids 29-38 of an HPV E6 protein, amino acids 52-61 of an HPV E6 protein, amino acids 129-138 of an HPV E6 protein, amino acids 137-146 of an HPV E6 protein, amino acids 149-158 of an HPV E6 protein, and amino acids 11-19 of an HPV E7 protein. E6 and E7 proteins being preferably from HPV16 or HPV18 as identified above by SEQ ID NO: 2, 3.

Each of the HPV peptides or epitopes identified herein is identified by providing the corresponding first amino acid and the corresponding last amino acid as identified in the corresponding E6 or E7 protein.

A preferred antigen comprises a peptide comprising a CD4 and/or CD8 T cell epitopes that are derived from the non-viral tumor antigen p53 as described in WO2008/147186, which publication is hereby incorporated by reference.

The amino acid sequence of human p53 is depicted in SEQ ID No. 7. Preferably, the length of the contiguous amino acid sequence derived from the protein p53 is no more than 45 amino acids and comprises at least 19 contiguous amino acids derived from the amino acid sequence of p53. The length of the contiguous amino acid sequence derived from p53 comprised within the peptide, preferably is 19-45, 22-45, 22-40, 22-35, 24-43, 26-41, 28-39, 30-40, 30-37, 30-35, 32-35, 33-35, 31-34 amino acids. In another preferred embodiment, a peptide comprises 22, 23, 24, 25, 26, 27, 28, 29, 30, 31, 32, 33, 34, 35, 36, 37, 38, 39, 40, 41, 42, 43, 44, or 45 or more than 45 contiguous amino acid residues of a p53. preferably from human p53 as identified above by SEQ ID NO:7. The skilled person will therefore understand that a peptide of the invention is distinct from a p53 protein, preferably from the human p53 as identified above by SEQ ID NO:7.

In a preferred embodiment, when the protein is human p53, as identified above by SEQ ID NO:7, the peptide is selected from the following peptides, each peptide comprises or consists of or overlaps with any of the following sequences: p53 86-115, p53 102-131, p53 142-171, p53 157-186, p53 190-219, p53 224-248, p53 225-254, p53 257-286, p53 273-302, p53 305-334, p53 353-382 and p53 369-393.

Even more preferably, when the protein is human p53, as identified above by SEQ ID NO:7, the peptide is selected from the following peptides, each peptide comprises or consists of or overlaps with any of the following sequences: p53 142-171, p53 157-186, p53 190-219, p53 224-248, p53 225-254, p53 241-270, p53 257-286 and p53 273-302.

Each of the p53 peptides identified herein is identified by providing the corresponding first amino acid and the corresponding last amino acid as identified in the corresponding human p53 protein as identified above by SEQ ID NO:7.

Preferred antigens include at least two of, or at least three of or the following p53 peptides: p53 142-171, p53 157-186, p53 190-219, p53 224-248, p53 225-254, p53 241-270, p53 257-286 and p53 273-302, p53 305-334, p53 353-382 and p53 369-393. More preferred antigens further include p53 86-115 and/or p53 102-131.

A preferred antigen comprises a peptide comprising a CD4 and/or CD8 T cell epitopes that are derived from the non-viral tumor antigen PRAME as described in WO2008/118017, which publication is hereby incorporated by reference.

Such peptide may comprise a contiguous amino acid sequence selected from the 509 amino acid sequence of the human PRAME protein, depicted in SEQ ID No. 8, whereby the peptide preferably comprises at least one HLA class II Th cell epitope and preferably also at least one HLA class I cytotoxic T cell epitope. Preferably, the length of the contiguous amino acid sequence from the human PRAME protein, preferably identified by SEQ ID NO:8, comprised within the peptide is 19-45, even more preferably 30-40 amino acids, even more preferably 30-35 and most preferably 33-35 amino acids. More preferred peptides comprise a contiguous amino acid sequence from the human PRAME protein preferably identified by SEQ ID NO:8 and selected from the group consisting of amino acid sequences, aa. 19-53, aa. 47-79, aa. 69-101, aa. 80-114, aa. 94-126, aa. 112-144, aa. 133-166, aa. 173-207, aa. 190-223, aa. 234-268, aa. 247-279, aa. 262-294, aa. 284-316, aa. 295-327, aa. 353-387, aa. 399-431, aa. 417-450, aa. 447-480, aa. 477-509. The invention also encompasses a peptide originating from PRAME as identified in this paragraph and comprising 1, 2, 3, 4, 5, 6, 7, 8, 9 or more additional amino acids in total derived from the corresponding positions of the corresponding PRAME protein. These additional amino acids may be present at the N and/or at the C terminal of said peptide. However, such peptides are preferably distinct from a full length PRAME protein identified by SEQ ID NO:8.

Each of the PRAME peptides identified herein is identified by providing the corresponding first amino acid and the corresponding last amino acid as identified in the corresponding human PRAME protein.

A preferred antigen comprises peptides comprising CD4 and/or CD8 T cell epitopes that are derived from the non-viral tumor antigen NY-ESO-1 as described in WO98/14464, which publication is hereby incorporated by reference.

A preferred antigen comprises peptides comprising CD4 and/or CD8 T cell epitopes that are derived from the non-viral tumor antigen XAGE-1 B as described in U.S. Pat. Nos. 6,630,574, 6,504,010, 7,425,607, 6,686,447, which publications are hereby incorporated by reference.

A preferred antigen comprises a peptide comprising a CD4 and/or CD8 T cell epitopes that are derived from the non-viral tumor antigen PSMA as described in EP11172914.1, which publication is hereby incorporated by reference.

Such peptide may comprise a contiguous amino acid sequence selected from the 750 amino acid sequence of the human PSMA protein, depicted in SEQ ID No. 9, whereby the peptide preferably comprises at least one HLA class II Th cell epitope and preferably also at least one HLA class I cytotoxic T cell epitope. Preferably, the length of the contiguous amino acid sequence from the human PSMA protein, preferably identified by SEQ ID NO:9, comprised within the peptide is 19-45, even more preferably 30-40 amino acids, even more preferably 30-35 and most preferably 33-35 amino acids. More preferred peptides comprise a contiguous amino acid sequence from the human PSMA protein preferably identified by SEQ ID NO:9 and selected from the group consisting of amino acid sequences, aa. 3-35, aa. 31-65, aa. 53-88, aa. 94-130, aa. 156-188, aa. 207-242, aa. 253-289, aa. 302-333, aa. 341-371, aa. 393-426, aa. 432-464, aa. 451-485, aa. 469-500, aa. 507-539, aa. 547-579, aa. 565-600, aa. 603-636, aa. 648-681, aa. 679-713, aa. 716-749. The invention also encompasses a peptide originating from PSMA as identified in this paragraph and comprising 1, 2, 3, 4, 5, 6, 7, 8, 9 or more additional amino acids in total derived from the corresponding positions of the corresponding PSMA protein. These additional amino acids may be present at the N and/or at the C terminal of said peptide. However, such peptides are preferably distinct from a full length PSMA protein identified by SEQ ID NO:9.

Each of the PSMA peptides identified herein is identified by providing the corresponding first amino acid and the corresponding last amino acid as identified in the corresponding human PSMA protein.

A preferred antigen comprises peptides comprising CD4 and/or CD8 T cell epitopes that are derived from the non-viral antigens derived from *Mycobacterium tuberculosis* as described in WO06/04389, which publication is hereby incorporated by reference.

An antigen derived from *Mycobacterium tuberculosis* is preferably selected from the group of polypeptides comprising *Mycobacterium* NRP/dormancy (DosR) regulon encoded proteins that are capable of eliciting an immune response in vivo in vertebrates having a *Mycobacterium* infection. More preferably, such antigen is from the group of polypeptides comprising *Mycobacterium* NRP/dormancy (DosR) regulon encoded proteins that are capable of eliciting an IFN-γ response in human T cell lines, consisting of Rv079, Rv0569, Rv0572c, Rv1733c, Rv1738, Rv1813c, Rv1996, Rv2007c (FdxA), Rv2029c (PfkB), Rv2030c, Rv2031c (HspX, Acr, 16-kDa alpha crystallin homolog), Rv2032, Rv2623, Rv2624c, Rv2626c, Rv2627c, Rv2628, Rv3126c, Rv3127, Rv3129, Rv3130c, Rv3131, Rv3132c, Rv3133c (DosR), Rv3134c, Rv0080, Rv1737c (NarK2), Rv1735c and Rv1736c (NarX). The Rv nomenclature for Mycobacterial antigens and the DNA and protein sequences of the NRP/dormancy (DosR) regulon are well known in the art and may for instance be found at: http://genolist.pasteur.fr/TubercuList/ or at http://www.ncbi.nlm.nih.gov/entrez (Accession number AL123456). The Rv nomenclature as used herein may refer to either the amino acid sequence of the antigen or the nucleotide sequence encoding the antigen.

The length of the contiguous amino acid sequence derived from the *Mycobacterium* protein is preferably no more than 45 amino acids and comprises at least 19 contiguous amino acids derived from the amino acid sequence of said *Mycobacterium* protein. The length of the contiguous amino acid sequence derived from said *Mycobacterium* protein comprised within the peptide, preferably is 19-45, 22-45, 22-40, 22-35, 24-43, 26-41, 28-39, 30-40, 30-37, 30-35, 32-35 33-35, 31-34 amino acids. In another preferred embodiment, a peptide comprises 22, 23, 24, 25, 26, 27, 28, 29, 30, 31, 32, 33, 34, 35, 36, 37, 38, 39, 40, 41, 42, 43, 44, or 45 or more than 45 contiguous amino acid residues of said *Mycobacterium* protein. The length of the contiguous amino acid sequence derived from said *Mycobacterium* protein comprised within the peptide may be the length of said peptide. The skilled person will therefore understand that a peptide of the invention may be distinct from said *Mycobacterium* protein.

The invention also encompasses a peptide originating from such protein as identified in this paragraph and comprising 1, 2, 3, 4, 5, 6, 7, 8, 9 or more additional amino acids in total derived from the corresponding positions of the corresponding protein. These additional amino acids may be present at the N and/or at the C terminal of said peptide. However, such peptides are preferably distinct from a full length *Mycobacterium* protein.

Within the context of the invention, peptide may comprise additional amino acids than the ones originating from an antigen or may entirely be made of or consist of an amino acid sequence originating from such antigen. The length of the contiguous amino acid sequence from one of the above-defined antigens comprised within the peptide, preferably is at least 19, 20, 21, 22, 23, 24, 25, 26, 27, 28, 29, 30, 31, 32, 33, 34, 35, 36, 37, 38, 39, 40, 41, 42, 43, 44 or 45 amino acids and/or preferably no more than 100, 99, 98, 97, 96, 95, 94, 93, 92, 91, 90, 89, 88, 87, 86, 85, 84, 83, 82, 81, 80, 60, 50, 45, 40, 35, 33 or 30 amino acids, more preferably the length of the contiguous amino acid sequence from one of the above-defined antigens comprised within the peptide is 19-45, even more preferably 22-40 amino acids, even more preferably 30-35 and most preferably 33-35 amino acids. In another preferred embodiment, the peptide of the invention consists of any of the contiguous amino acid sequence from the antigen as defined herein, whereby it is understood that no amino acids are appended to either end of the contiguous amino acid sequence from the antigen that are not contiguous with this amino acid sequence in the sequence of the native antigen. These peptides may be easily synthesized and are large enough to be taken up by professional antigen presenting cells, processed by the proteasome and other proteases and peptidases of the intracellular processing system, and have sufficient physical capacity and length to contain at least one HLA class I and/or at least one HLA class II epitope. Optionally a peptide may comprise N- or C-terminal extensions, which may be additional amino acids, modified amino acids or other functional groups that may for instance enhance bio-availability, cellular uptake, targeting to T-cells, processing and/or solubility or comprise or release immune modulating substances that provide adjuvant or (co)stimulatory functions.

The compound of the invention is preferably expected to behave as an adjuvant. An adjuvant is defined herein as a molecule which is able to stimulate the immune system in such a way that an immune response, or an increase thereof, is elicited against said antigen when the antigen is administered in combination with the adjuvant (as a single compound or as two separate molecules as defined herein). To analyze or assess the antigen-specific elicited immune response, said immune response is compared to the immune response induced in presence of the antigen without the adjuvant or in the presence of the antigen with a known adjuvant. A known adjuvant may be another TLR2 adjuvant as identified in the experimental part as Pam3CysSK4. The induction is assessed in a subject or in cells from a subject.

Without wishing to be bound by any theory, a compound of the invention is believed to act via TLR2.

An immune response induced or elicited may be a B and/or T cell response. An immune response may be a B cell response, i.e. production of an antibody specifically directed against said antigen. An antibody is preferably an IgG antibody. Said immune response may be a T cell response. Said B and/or T cell response may be detected by measuring the production of antibody and/or cytokine using an ELISA as described in the example. Preferred cytokines are IFNγ, IL-2, IL-4, IL-5, TNFα or IL-10.

In a preferred embodiment, the detection of the antigen-specific elicited immune response means that said detection occurs after at least one, ten, eleven, twelve hours or more or after at least one day of administration of said adjuvant and antigen, or at least two days, or at least three days, or at least four days, or at least five days, or at least six days, or at least seven days, or at least two weeks, or at least three weeks, or at least 4 weeks or more. The detection is assessed in a subject or in cells from a subject.

In the context of the invention, the antigen-specific elicited immune response preferably means a detectable increase of an immune response against said antigen. Said detectable increase may be assessed by comparison with the immune response induced or elicited when the antigen is used alone or when said antigen is used with a known adjuvant. A known adjuvant may be another TLR2 adjuvant as identified in the experimental part (Pam3CysSK4). A detectable increase is preferably an increase of at least 5% of the amount of a cytokine as already identified herein, or 10%, 15%, 20%, 25%, 30%, 35%, 40%, 45%, 50%, 55%, 60%, 65%, 70%, 75%, 80%, 85%, 90%, 95%, 100%, 150%, 200% or more after at least one, ten, eleven, twelve hours or more or after at least one day of administration of said adjuvant and antigen, or at least two days, or at least three days, or at least four days or more. The detection is assessed in a subject or in cells from a subject.

The functionality of the compound of the invention may also be assessed as described in the experimental part using a cell expressing TLR2.

Surprisingly, it appears that the compound of the invention is able to induce at least a similar or even a more potent immune response against a given antigen using a dose of said compound which is lower than classically used dose of adjuvant. Lower may mean a dose which is at least 1 fold, at least 10 fold, at least 30 fold, at least 50 fold, at least 100 fold, at least 150 fold or at least 200 fold lower than the one of a classical adjuvant as Pam3CysSK4).

The vaccine composition of the present invention can additionally include, in addition to the adjuvant and an antigen, one or more effective ingredients having the same or similar effect with them. For example the vaccine composition according to the invention may comprise one or more adjuvants, in addition to the adjuvant according to the present invention. These other adjuvants may be admixed to the vaccine composition according to the invention or may be administered separately to the mammal or human to be treated. Examples of suitable other adjuvants to be used in combination with the adjuvant compound according to the invention are Montanide adjuvant, such as Montanide ISA-51 or Montanide ISA 720 (Seppic France), Freund's adjuvant or IFA, Resiquimod; imiquimod; Poly IC:LC (Hiltonol); ISCOMS; CpG and GLA; MPL. Another adjuvant is a T cell adhesion inhibitor, more preferably an inhibitor of an endothelin receptor such as BQ-788 (Buckanovich R J et al, Ishikawa K, PNAS (1994) 91:4892). BQ-788 is N-cis-2,6-dimethylpiperidinocarbonyl-L-gamma-methylleucyl-D-1-methoxycarbonyltryptophanyl-D-norleucine. However any derivative of BQ-788 or modified BQ-788 compound is also encompassed within the scope of this invention.

The vaccine composition may also comprise compounds like for example detoxified Lipid A, clinical grade CpG or other appropriate immunomodulatory agent or antibody such as CTLA-4 blocking or CD40 agonistic antibodies or agonistic antibodies against other members of the TNF receptor family such as OX40, CD27, 4-1-BB (CD137) or 4-1-BB and/or CD40 ligands, OX40 ligands or functional fragments and derivates thereof, as well as synthetic compounds with similar agonistic activity. These compounds can be mixed or conjugated to either the compound according to the invention and/or to the specific antigen in the vaccine.

The vaccine composition can also include, in addition to the above-mentioned effective ingredients, one or more pharmaceutically acceptable carriers for the administration. The pharmaceutically acceptable carrier can be selected or be prepared by mixing more than one ingredients selected from a group consisting of saline, sterilized water, Ringer's solution, buffered saline, dextrose solution, maltodextrose solution, glycerol and ethanol. Other general additives such as anti-oxidative agent, buffer solution, bacteriostatic agent, etc., can be added. In order to prepare injectable solutions such as aqueous solution, suspension and emulsion, diluents, dispersing agents, surfactants, binders and lubricants can be additionally added.

The specific formulation of the vaccine composition of the present invention, ways of administration and the use of pharmaceutically acceptable excipients are known in the art and for instance described in Remington; The Science and Practice of Pharmacy, 21st Edition 2005, University of Sciences in Philadelphia. Vaccine compositions and medicaments of the invention are preferably formulated to be suitable for intravenous or subcutaneous, or intramuscular administration, although other administration routes can be envisaged, such as mucosal administration or intradermal and/or intracutaneous administration, e.g. by injection or via a patch. Intradermal administration is preferred herein.

In a preferred embodiment, the vaccine composition is formulated to be suitable for intradermal administration or application. Intradermal is known to the skilled person. In the context of the invention, intradermal is synonymous with intracutaneous and is distinct from subcutaneous. A most superficial application of a substance is epicutaenous (on the skin), then would come an intradermal application (in or into the skin), then a subcutaneous application (in the tissues just under the skin), then an intramuscular application (into the body of the muscle).

The intradermal administration of the vaccine composition is very attractive since the injection of the vaccine is realized at or as close by as possible to the site of the disease resulting in the local activation of the disease draining lymph node, resulting in a stronger local activation of the immune system. In a preferred embodiment, the intradermal administration is carried out directly at the site of the lesion or disease. At the site of the lesion is herein understood to be within less than 5, 2, 1, 0.5, 0.2 or 0.1 cm from the site of the lesion.

In addition, a preferred embodiment comprises delivery of the antigen and adjuvant compound as part of the vaccine composition in a slow release vehicle such as mineral oil (e.g. Montanide ISA 51), PLGA based particles or scaffolds, dextran based particles or scaffolds, poly active based particles or scaffolds, liposomes, virosomes. Preferably for intradermal delivery the vaccine composition is administered in a composition comprising in addition one or more immunologically inert pharmaceutically acceptable carriers, e.g. buffered aqueous solutions at physiological ionic strength and/or osmolarity (such as e.g. PBS).

It is furthermore encompassed by the present invention that the administration of at least one vaccine composition of the invention may be carried out as a single administration. It may also be possible that the various active compounds of the vaccine are administered sequentially and/or using different ways or different sites of administration. Alternatively, the administration of at least one vaccine composition may be repeated if needed.

DEFINITIONS

In the context of the invention, an antigen may be defined by a peptide. Any peptide overlapping with such initial peptide is also encompassed by the present invention. Overlapping means that the sequence of the peptide partially or completely overlaps with a given sequence. Preferably, overlapping means partially overlapping. Partially preferably means that the overlap is of one or more amino acids at the N-terminus and/or at the C-terminus of the peptide sequence, more preferably of two or more amino acids at the N-terminus and/or at the C-terminus, or more. It is also preferred that the overlap is of one or more amino acids at the N-terminus and/or two or more amino acids at the C-terminus of the peptide sequence or vice versa. The skilled person will understand that all kinds of overlaps are encompassed by the present invention as long as the obtained peptide exhibits the desired activity as earlier defined herein.

In the context of the invention, a peptide is represented by an amino acid sequence.

In the context of the invention, a nucleic acid molecule is represented by a nucleic acid or nucleotide sequence which encodes a peptide. A nucleic acid molecule may comprise a regulatory region.

It is to be understood that each nucleic acid molecule or protein or peptide as identified herein by a given Sequence Identity Number (SEQ ID NO) is not limited to this specific sequence as disclosed.

Throughout this application, each time one refers to a specific amino acid sequence SEQ ID NO of a peptide, one may replace it by a peptide comprising an amino acid sequence that has at least 60%, 65%, 70%, 75%, 80%, 85%, 90%, 95%, 97%, 98%, 99% or 100% sequence identity or similarity with amino acid sequence with a given SEQ ID NO.

In a preferred embodiment, sequence identity or similarity is determined by comparing the whole length of the sequences as identified herein.

"Sequence identity" is herein defined as a relationship between two or more amino acid (polypeptide or protein or peptide) sequences or two or more nucleic acid (polynucleotide) sequences, as determined by comparing the sequences. In a preferred embodiment, sequence identity is calculated based on the full length of two given SEQ ID NO or on part thereof. Part thereof preferably means at least 50%, 60%, 70%, 80%, 90%, or 100% of both SEQ ID NO. In the art, "identity" also means the degree of sequence relatedness between amino acid or nucleic acid sequences, as the case may be, as determined by the match between strings of such sequences.

"Similarity" between two amino acid sequences is determined by comparing the amino acid sequence and its conserved amino acid substitutes of one polypeptide to the sequence of a second polypeptide. "Identity" and "similarity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps).

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to Ser; Arg to Lys; Asn to Gln or His; Asp to Glu; Cys to Ser or Ala; Gln to Asn; Glu to Asp; Gly to Pro; His to Asn or Gin; Ile to Leu or Val; Leu to Ile or Val; Lys to Arg; Gln or Glu; Met to Leu or Ile, Phe to Met, Leu or Tyr; Ser to Thr; Thr to Ser; Trp to Tyr; Tyr to Trp or Phe; and, Val to Ile or Leu.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a compound or a composition as defined herein may comprise additional component(s) than the ones specifically identified, said additional component(s) not altering the unique characteristic of the invention.

In addition, reference to an element by the indefinite article "a" or "an" does not exclude the possibility that more than one of the elements is present, unless the context clearly requires that there be one and only one of the elements. The indefinite article "a" or "an" thus usually means "at least one".

All patent and literature references cited in the present specification are hereby incorporated by reference in their entirety.

The invention shall be illustrated by the following non-limiting examples.

EXAMPLE 1

To illustrate the advantages of the compounds according to the invention two variants of the established TLR2/TLR1 ligand $Pam_3CysSK_4$ containing the $CH_2$ to NH substitution were prepared. These two compounds named U-Pam-14 and U-Pam-12 differ in the length of the fatty chain attached to the N-terminus of the Cys residue, U-Pam-14 being an exact isostere of palmitoyl moiety of the natural ligand while UPam-12 contains a shortened chain. FIG. 1 shows the state of the art $Pam_3CysSK_4$ ligand and the U-Pam-14 and U-Pam-12 ligand according to the invention. A circle shows where the —$CH_2$— bridge has been replaced by the —NH-bridge.

All reagents and solvents used in the solid phase peptide synthesis were purchased from Bachem and Biosolve and used as received. Fmoc-Cys((RS)-2,3-di(palmitoyloxy)-propyl)-OH (herein, (RS) denotes a mixture of R- and S-epimers at C-2 of the dipalmitoyloxypropyl group) was purchased from Bachem, Fmoc-amino acids, HCTU and PyBOP from Novabiochem. Tentagel based resins were ordered from Rapp Polymere. LC/MS was conducted on a JASCO system using a Vidac C4 analytical column (4.6×50 mm, 5 μm particle size, flow 1.0 mL/min.) or an Alltima CN analytical column (4.6×50 mm, 3 μm particle size, flow 1.0 mL/min.). Absorbance was measured at 214 and 256 nm.

Solvent system:
A: 100% water,
B: 100% acetonitrile,
C: 1% TFA/H2O.

Gradients of B in 10% C were applied over 15 minutes unless stated otherwise. Purifications were conducted on the Gilson preparative HPLC system, supplied with a semi preparative Vidac C4 column (10×250 mm, 5 μm particle size, flow 5.0 mL/min.).

Solvent system:
A: 100% water,
B: 100% acetonitrile,
C: 1% TFA/H2O.

Gradients of B in 10% C were applied over 3 CV unless stated otherwise. The UV absorption was measured with 214 and 256 nm. The solid-phase peptide synthesis was performed on an ABI (Applied Biosystems) 433A automated instrument applying Fmoc based protocol starting from Tentagel-RAM resin according to established methods. The consecutive steps performed in each cycle applied for Fmoc-Lys(Boc)-OH were:

1) Deprotection of the Fmoc-group with 20% piperidine in NMP for 15 min;
2) NMP wash;
3) Coupling of the appropriate amino acid using a five-fold excess.

Briefly, the Fmoc amino acid (0.25 mmol) was dissolved in 0.25 M HCTU in NMP (1 mL), the resulting solution was transferred to the reaction vessel followed by 0.5 mL of 1.0 M DIPEA in NMP to the initiate the coupling. The reaction vessel was then shaken for 45 min;

4) NMP wash;
5) capping with 0.5 M acetic anhydride in NMP in presence of 0.5 mmol DIPEA;
6) NMP wash;
7) Final Fmoc removal with 20% piperidine in NMP for 15 min;
8) NMP wash;
9) DCM wash.

H-Ser(tBu)-Lys(Boc)-Lys(Boc)-Lys(Boc)-Lys(Boc)-

Rink-Tentagel (1)

Peptide synthesis was performed on a 1 mmol scale using an ABI 433A automated instrument applying Fmoc based protocol starting form Rink Amide S Tentagel (loading 0.26 mmol/g). The resin, after final Fmoc deprotection, was washed with NMP and DCM and dried. The resulting resin 1 was used in the next step.

General procedure coupling Fmoc-Cys((RS)-2,3-di(palmitoyloxy)-propyl)-OH

The Tentagel S Ram resin 1 loaded with H-Ser(tBu)-Lys(Boc)-Lys(Boc)-Lys(Boc)-Lys(Boc)-Rink-Tentagel was treated with a 0.5 mL stock solution of 0.18 M Fmoc-Cys((RS)-2,3-di(palmitoyloxy)-propyl)-OH in 0.22 M PyBop in DCM:NMP (2:1). The resulting mixture was activated with 2×44 μmol Dipea over 15 min. and reacted by shaking for 18 h followed by NMP and DCM wash. The resin was swelled in DCM:NMP again and divided in portions of 10 μmol.

General Procedure for Isocyanate Addition

The 10 μmol resin loaded with Fmoc-Cys((RS)-2,3-di(palmitoyloxy)-propyl)-Ser(tBu)-Lys(Boc)-Lys(Boc)-Lys(Boc)-Lys(Boc) 2 was swelled in DCM:NMP (1:1) and treated with 3×3 min 20% piperidine in NMP for Fmoc-deprotection. After a thorough NMP wash the resin was suspended in 1 mL DCM:NMP (1:1) and treated with tetradecyl isocyanate or dodecyl isocyanate (25 μL). The mixture was shaken for 18 h, washed with NMP and DCM and air dried. The resin was treated for 104 minutes with a cleavage cocktail TFA/TIS/$H_2O$ (95/2.5/2.5). The solution was filtered and precipitated with $Et_2O$ (50 mL) and stored at −200° C. for 18 h. The Et$_2$O was centrifuged, removed and the precipitated was dissolved by sonification in 1 ml MeCN:H$_2$O:tBuOH (1:1:1). Of each 50 µL product was diluted with 50 µL MeCN:H$_2$O:tBuOH (1:1:1) for LCMS analysis (Vidac C4 column). Obtained sequences were diluted with another 0.5 mL MeCN:H$_2$O:tBuOH (1:1:1) and were purified on a semipreparative Vidac C4 column (10× 250 mm, 5 µm particle size, flow 5.0 mL/min, 60-100% B.).

The thus obtained compounds according to the invention had the following properties:

| Upam-14: |
|---|
| 1-tetradecyl-urea-Cys((RS)-2,3-di(palmitoyloxy)-propyl)-Ser-Lys-Lys-Lys-Lys-NH$_2$ (*) was obtained: |
| 0.89 mg (0.59 µmol, 6%), |
| LCMS: 50-90% B, |
| rt 8.23 min. |
| Bruto formula C$_{80}$H$_{156}$N$_{12}$O$_{12}$S calculated 1509.17, found ESI-MS: |
| [M + H]$^+$: 1510.6 (calculated 1510.2), [M + H]2+: 756.0 (calculated 755.8). |
| HRMS [M + H+] calcd for C$_{80}$H$_{156}$N$_{12}$O$_{12}$S 1510.17592, found 1510.17670. |

(*) RS denotes a mixture of epimers at C-2 of the dipalmitoyloxypropyl group.

| Upam-12 |
|---|
| 1-dodecadecyl-urea-Cys((RS)-2,3-di(palmitoyloxy)-propyl)-Ser-Lys-Lys-Lys-Lys-NH$_2$ (*) |
| 0.89 mg (0.59 µmol, 6%), |
| LCMS: 50-90% B |
| rt 8.06 min. |
| Bruto formula C$_{79}$H$_{154}$N$_{12}$O$_{12}$S calculated 1495.15, found ESI-MS: |
| [M + H]+: 1496.3 (calculated 1496.16). |

(*) RS denotes a mixture of epimers at C-2 of the dipalmitoyloxypropyl group.

EXAMPLE 2

Figure 3A:
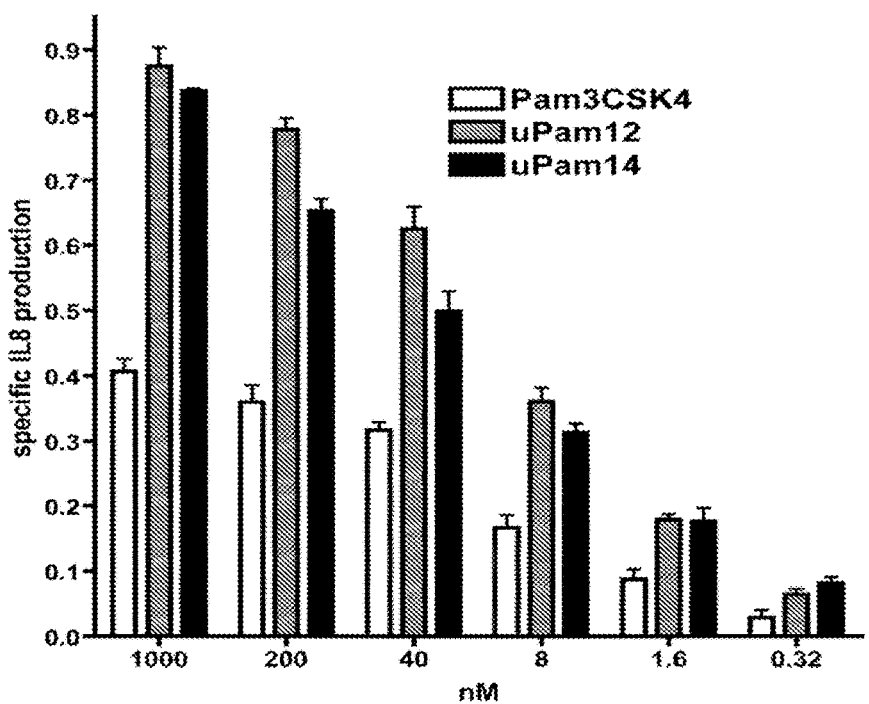
FIGS. 3A and 3B show the test results wherein TRL2-transfected HEK cells and dendritic cells were incubated with the state of the art compounds and compounds according to the invention.
Figure 3B:
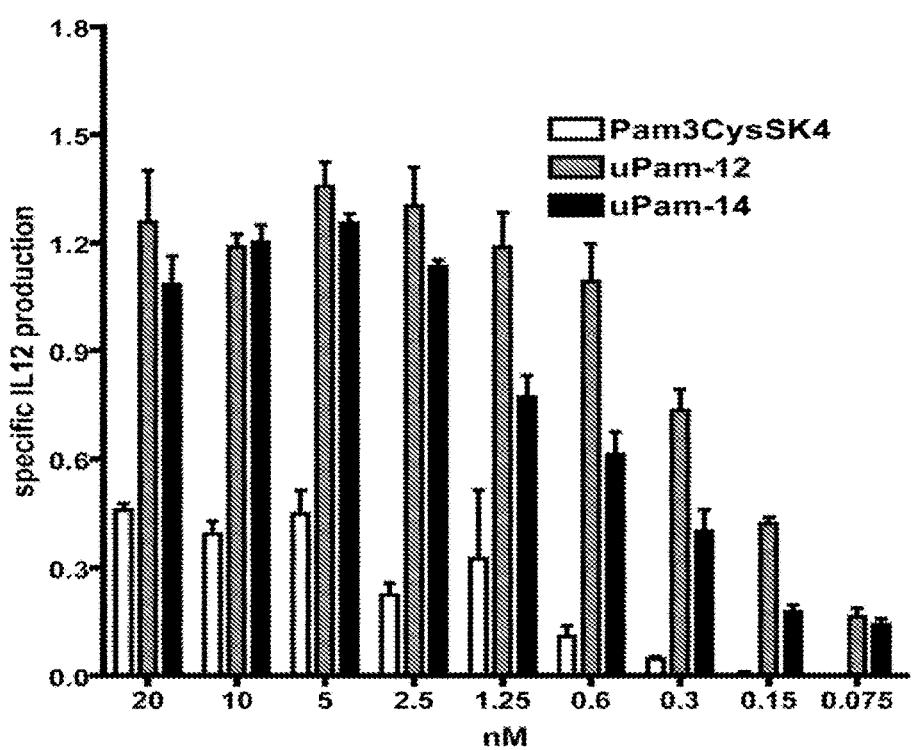

The two compounds U-Pam-12 and U-Pam-14 as obtained in Example 1 were tested in comparison to unmodified Pam3CysSK4 for their functional capacity to activate a human TLR2 expressing reporter cell line HEK-TLR2 (FIG. 3A) and a murine dendritic cell line (FIG. 3B).

In the test live TLR2-transfected HEK cells and dendritic cells (5×10$^4$ cells/well) were incubated with titrating concentrations of the respective Pam compounds in culture medium and incubated at 37° C. After 24 hours, supernatants were harvested and the presence of IL-8 or IL-12 cytokines respectively, was measured by specific sandwich ELISA assays.

Both cell types were significantly more stimulated by the U-Pam compounds than the unmodified Pam3CysSK4. Both compounds increased the maximal stimulation level at least twofold and were calculated to be at least 100-fold more effective as based on the concentration of the compound needed to reach similar stimulation levels.

It was found that the compound according to the invention can functionally stimulate TLR2 from both human and mouse origin in low (pM to nM) concentrations. The active concentrations are lower than those of the unmodified TLR2 ligand. Additionally, the physiologically important dendritic cells can be activated to produce the immunologically relevant cytokine IL-12. This cytokine is crucially important to facilitate efficient priming of specific T lymphocytes to viruses and/or tumor-antigens. Therefore, a composition comprising said compound as adjuvant can effectively be used to increase the immunogenicity of antigen and thereby improving the efficacy of a vaccine.

It is believed that the use of a compound according to the invention will result in an improved immune response, meaning a more robust innate immune system activation as well as a more robust adaptive immune system activation, expressed in a higher T cell response and/or a higher antibody response, in comparison to immune stimulation with the known Pam3Cys-SK4.

EXAMPLE 3

This example illustrates the synthesis of a UPam-14 derivative in which R$^5$ group (CH$_2$—OH) is replaced by CH$_2$—CH$_3$. This compound named here Upam-14-Abu.

H-Abu-Lys(Boc)-Lys(Boc)-Lys(Boc)-Lys(Boc)-Rink-Tentagel (2)

Peptide synthesis was performed as described in Example 1 for H-Ser(OtBu)-Lys(Boc)-Lys(Boc)-Lys(Boc)-Lys(Boc)-Rink-Tentagel (1) with the only difference that Fmoc-Abu-OH was applied instead of Fmoc-Ser(OtBu)-OH to introduce 2-aminobutyric acid residue instead of serine residue of Upam-14. Subsequent synthetic and purification steps were identical to those described in Example 1.

The thus obtained compound according to the invention had the following properties:

| Upam-14-Abu |
|---|
| 1-tetradecyl-urea-Cys((RS)-2,3-di(palmitoyloxy)-propyl)-Abu-Lys-Lys-Lys-Lys-NH2 |
| 3.22 mg (2.13 µmol, 21%), |
| LCMS: 50-90% B |
| rt 8.31 min. |
| Bruto formula C81H158N12O11S calculated 1507.19, found ESI-MS: |
| [M + H]+: 1508.5 (calculate 1508.2), [M + H]2+: 755.1 (calculated 754.6). |
| HRMS [M + H+] calcd for C81H158N12O11S 1508.19665, found 1508.19725. |

EXAMPLE 4

Figure 5A:
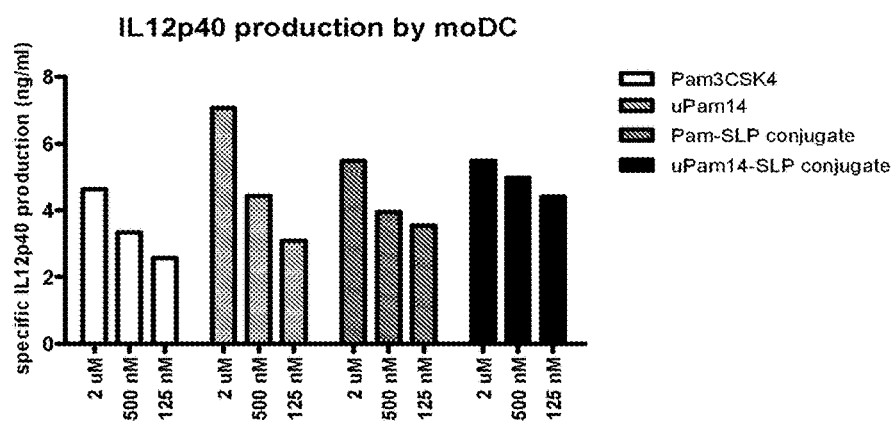
FIGS. 5A, 5B, and 5C show the results of activation of human monocyte-derived dendritic cells (moDC).
Figure 5B:
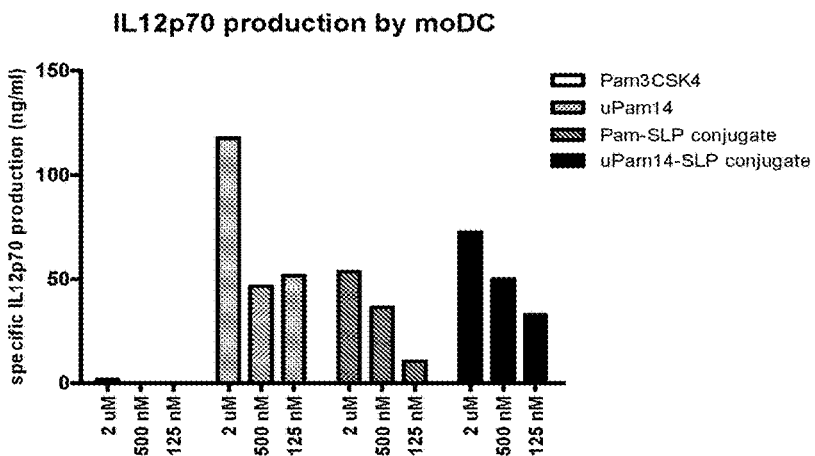
Figure 5C:
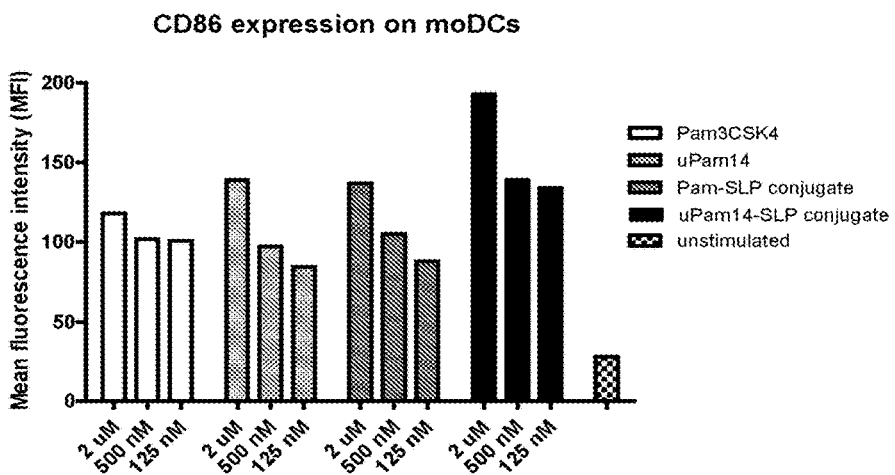
Figure 6A:
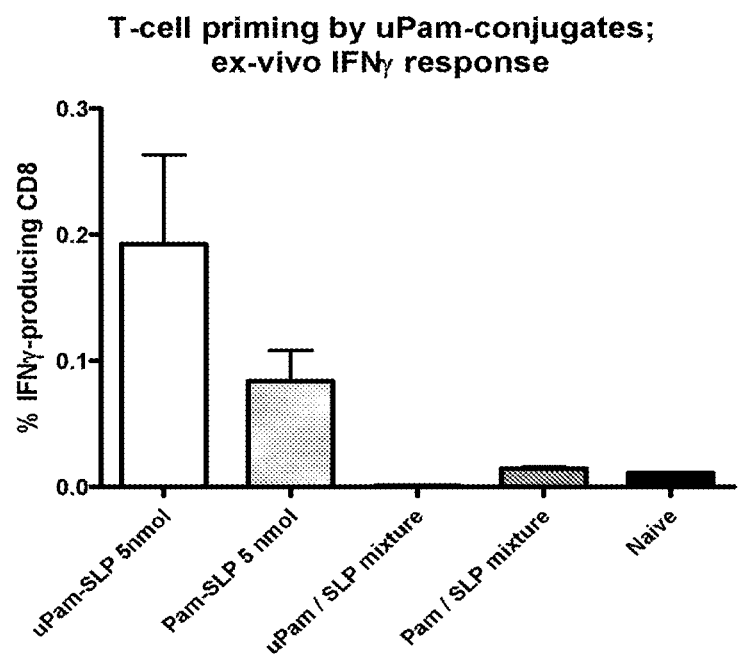
FIGS. 6A and 6B show the in vivo T cell priming capacity of the U-Pam conjugated synthetic long peptide of the OVA antigen (containing the SIINFEKL CTL epitope).
Figure 6B:
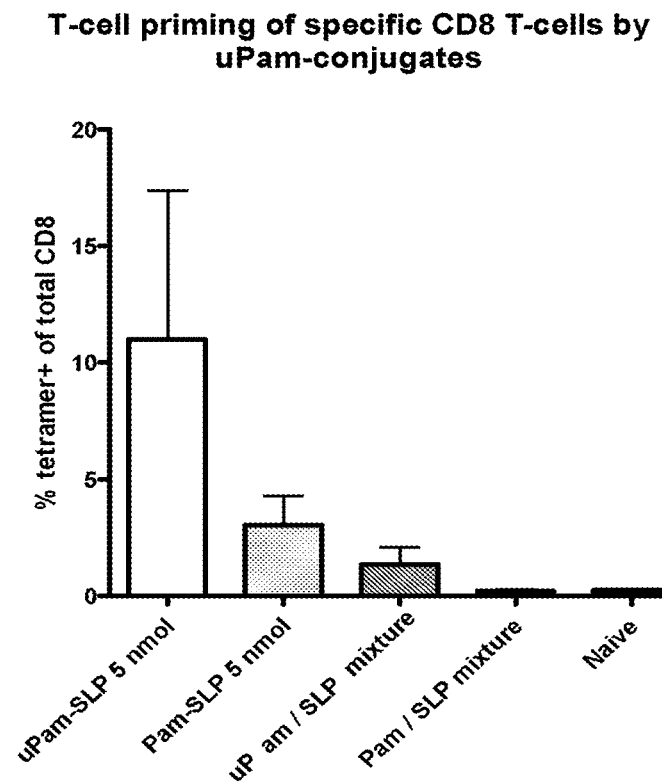

The U-Pam compound was further functionally tested in dendritic cells (FIGS. 4, 5A, 5B and 5C) and in vivo in mice (FIGS. 6A and 6B).

Figure 4:
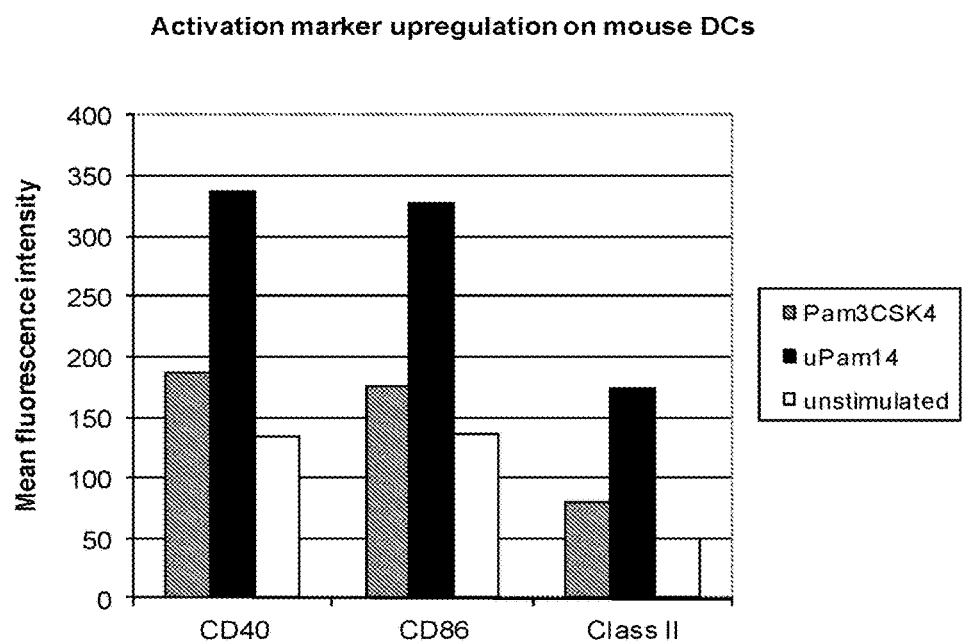
FIG. 4 shows the test results for a murine DC cell line which were incubated with the state of the art compounds, compounds according to the invention or left unstimulated.

FIG. 4 shows a murine DC cell line which was incubated for 48 hours with 30 nM of either U-Pam3CSK4 (U-Pam14) or Pam3CSK4, or left unstimulated. The DCs were subsequently stained with antibodies directed against CD40, CD86 and MHC class II molecules. Mean fluorescence intensity was determined FACS analysis. These data show that U-Pam is superior to wt Pam not only in IL-12 cytokine production (see example 2) but also in expression of cell surface molecules which are hallmarks for optimal DC maturation related to optimal T cell priming capacity.

FIGS. 5A, 5B, and 5C show the analysis of U-Pam activation of human monocyte-derived dendritic cells (moDC). On day 5 of culturing the CD14+ fraction of donor PBMC in growth medium with IL-4 and GM-CSF, these moDC were incubated with either wt Pam3CSK4, U-Pam14, Pam3CSK4-conjugated or U-Pam14-conjugated synthetic long peptide (Pam-SLP or uPam14-SLP), or left unstimulated. After 48 hours of incubation, the supernatant of the moDC cultures was taken, which was subjected to IL12p40

(FIG. 5A) and IL12p70 (FIG. 5B) ELISA analysis. After 48 hours of incubation, the moDCs were stained with antibodies directed against CD86 (FIG. 5C). This analysis shows that the U-Pam compound also improves activation of human dendritic cells. Importantly, not only the free compound but also the U-Pam conjugated to long peptide antigen improved DC activity.

In vivo T cell priming capacity of the U-Pam conjugated synthetic long peptide of the OVA antigen (containing the SIINFEKL CTL epitope) is shown in FIGS. 6A and 6B. C57BL/6 mice were vaccinated subcutaneously with either 5 nmol U-Pam14-SLP conjugate, 5 nmol of Pam3CSK4-SLP conjugate, 5 nmol of free U-Pam14 mixed with 5 nmol of SLP, 5 nmol of free Pam3CSK4 mixed with 5 nmol of SLP, or with PBS only. After 14 days, mice were sacrificed and spleens were harvested and a single cell suspension was made. The splenocytes were intracellularly stained with fluorescently labeled antibodies directed against interferon-γ, and with antibodies directed against cell-surface markers CD3 and CD8 β. The percentage of IFNγ producing OVA peptide-specific CD8 T cells is shown (FIG. 6A). In another independent experiment C57BL/6 were vaccinated as described above and again after 14 days spleens were harvested. A fraction of the splenocytes was restimulated for 7 days with irradiated OVA-expressing EG7 lymphoma cells. The cultured splenocytes were stained with MHC class I Kb-SIINFEKL-APC tetramers, and with antibodies directed against cell surface markers CD3 and CD8 β. The percentage of OVA-specific CD8 T cells is shown in (FIG. 6B). Both in vivo experiments show enhanced priming of antigen-specific CD8 T cells by conjugation of Upam14 to SLP which harbors a T cell epitope.

EXAMPLE 5

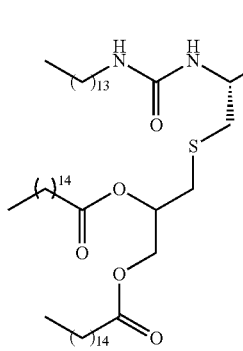

The UPam variants wherein $X_n$ was varied were compared by measuring IL-12 production and the up-regulation of the cell surface markers CD40, CD86 and MHC Class II at 3 µM and 30 nM. Herein, $X_n$ takes the place of serine in the $SK_4$ peptide part according to formula (2), containing different groups for $R^5$. Compounds X1 up to X8 containing these different groups $R^5$, which were studied are listed in the table below, wherein X1 is the UPam-14 as prepared in Example 1 and X2 is the UPam-14-Abu as prepared in Example 3. The potency of the compounds to upregulate CD40 followed the trend as observed in the DC maturation assay. The compounds X1, X2, X3, X4, X5, X6, X7 or X8 showed an increased amount of up-regulation as compared to the results obtained with the state of the art $Pam_3Cys$-$SK_4$. In the up-regulation of the cell surface marker CD86 and MHC class II a corroborated trend was observed.

| Compound | $R^5$ |
|---|---|
| X1 | HO– |
| X2 | –CH₂CH₃ |
| X3 | –propyl |
| X4 | –butyl |
| X5 | –CH₂CH=CH₂ |
| X6 | –C≡CH |
| X7 | –CH₂CH₂NH₂ |
| X8 | –OCH₂C(O)NH₂ |

The invention claimed is:

1. A compound represented by the following formula [1]:

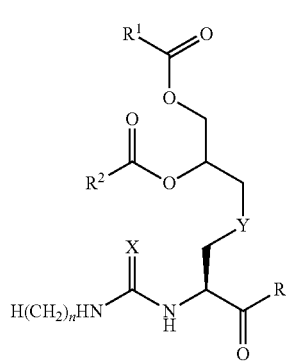

[1]

wherein $R^1$ and $R^2$ are each independently a branched or straight group having up to 17 atoms selected from carbon, nitrogen, oxygen and sulphur, n is 0 to and including 18, Y is sulphur or selenium, X is S or O and R is selected from the group consisting of an organic group comprising one or more peptides, one or more nucleic acids, one or more antibodies, and combinations thereof.

2. The compound according to claim 1, wherein X is O.

3. The compound according to claim 1, wherein Y is sulphur.

4. The compound according to claim 1, wherein $R^1$ and $R^2$ are each independently a straight chain alkyl group having 10 to 17 carbon atoms.

5. The compound according to claim 4, wherein $R^1$ and $R^2$ are straight chain alkyl groups having 15 carbon atoms.

6. The compound according to claim 1, wherein n is 11 to and including 15.

7. The compound according to claim 1, wherein R is an organic group comprising one or more peptides, and wherein R is optionally coupled to an antigen.

8. The compound according to claim 7, wherein R is $SK_m$ and wherein m is 1, 2, 3, 4 or 5.

9. The compound according to claim 7, wherein group R is represented by

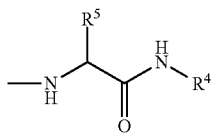

in which R⁴ is a $K_m$ peptide part, wherein m is 0, 1, 2, 3, 4 or 5, and wherein R⁴ is optionally coupled to an antigen and in which R⁵ is hydrogen or a group comprising one to six atoms chosen from carbon, nitrogen and oxygen.

10. The compound according to claim 9, wherein R⁵ is a —CH₂—OH group, a —CH₂—CH₃ group, a —(CH₂)₃—CH₃ group, a —CH₂C≡CH group, a —CH₂CH=CH₂ group or a —(CH₂)₂NH₂ group.

11. The compound according to claim 9, wherein R⁵ is not hydrogen and the asymmetric carbon to which R⁵ is attached has the L configuration.

12. The compound according to claim 9, wherein the $K_m$ peptide part is coupled to an antigen, a nucleic acid and/or an antibody.

13. A solid phase peptide synthesis process to prepare a compound according to claim 1, comprising
   (a) providing R-H, which is optionally immobilized and/or side-chain protected;
   (b) coupling of substituted cysteine building block Fmoc-(Y-(2-(OC(O)R²)-3-(OC(O)R¹))propyl)-Cys-OH to R-H; and
   (c) cleaving the Fmoc-group from the N-terminus of the resulting peptide; and
   (d) treating the Fmoc-liberated peptide with H—(CH₂)ₙ—N=C=X,
wherein R, R¹, R², X, Y and n are defined as in claim 1.

14. The process according to claim 13, wherein R is an organic group comprising one or more peptides and R-H is immobilized and/or side-chain protected.

15. The process according to claim 14, further comprising:
   (e) conjugating an antibody or a nucleic acid to the H—(CH₂)ₙ—N=C=X-treated peptide.

16. A composition comprising the compound according claim 1 and an antigen.

17. The composition according to claim 16, wherein the antigen is conjugated to the compound.

18. The composition according to claim 16, which is a vaccine against the antigen.

19. A method for the induction, maintenance and/or enhancement of an immune response in a subject against an antigen and/or for the prevention, delay and/or treatment of a disease or condition associated with an antigen in a subject, comprising administering to the subject a composition comprising a compound according to claim 1 and an antigen.

20. The method according to claim 19, wherein the antigen is conjugated to the compound.

21. The compound according to claim 4, wherein R¹ and R² are straight chain alkyl groups having 15 carbon atoms, m is 4, n is 12 or 14, X is O, and Y is sulphur.

* * * * *